(12) United States Patent
Atkinson et al.

(10) Patent No.: US 6,402,750 B1
(45) Date of Patent: Jun. 11, 2002

(54) DEVICES AND METHODS FOR THE TREATMENT OF SPINAL DISORDERS

(75) Inventors: Robert E. Atkinson, Falcon Heights; Peter T. Keith, Saint Paul, both of MN (US)

(73) Assignee: SpinLabs, LLC, Stillwater, MN (US)

( * ) Notice: Subject to any disclaimer, the term of this patent is extended or adjusted under 35 U.S.C. 154(b) by 0 days.

(21) Appl. No.: 09/542,972

(22) Filed: Apr. 4, 2000

(51) Int. Cl.$^7$ .............................................. A61B 17/70
(52) U.S. Cl. ...................................... 606/61; 623/17.16
(58) Field of Search ........ 606/60, 61; 623/17.11–17.16

(56) References Cited

U.S. PATENT DOCUMENTS

| | | | |
|---|---|---|---|
| 4,743,260 A | 5/1988 | Burton | 623/17 |
| 5,047,055 A * | 9/1991 | Bao et al. | 623/17 |
| 5,092,866 A | 3/1992 | Breard et al. | 606/61 |
| 5,171,280 A * | 12/1992 | Baumgartner | 623/17 |
| 5,180,393 A | 1/1993 | Commarmond | 623/13 |
| 5,192,326 A * | 3/1993 | Bao et al. | 623/17 |
| 5,201,729 A | 4/1993 | Hertzmann et al. | 606/2 |
| 5,306,310 A | 4/1994 | Siebels | 623/17 |
| 5,375,823 A | 12/1994 | Navas | 267/195 |
| 5,415,661 A | 5/1995 | Holmes | 606/69 |
| 5,433,739 A | 7/1995 | Sluijter et al. | 607/99 |
| 5,480,401 A | 1/1996 | Navas | 606/61 |
| 5,496,318 A | 3/1996 | Howland et al. | 606/61 |
| 5,534,028 A * | 7/1996 | Bao et al. | 623/17 |
| 5,549,679 A * | 8/1996 | Kuslich | 623/17 |
| 5,562,737 A | 10/1996 | Graf | 623/17 |
| 5,645,597 A * | 7/1997 | Krapiva | 623/17 |
| 5,645,599 A | 7/1997 | Samani | 623/17 |
| 5,672,175 A | 9/1997 | Martin | 606/61 |
| 5,716,416 A | 2/1998 | Lin | 623/17 |
| 5,728,097 A | 3/1998 | Mathews | 606/61 |
| 5,755,797 A | 5/1998 | Baumgartner | 623/17 |
| 5,785,705 A | 7/1998 | Baker | 606/32 |
| 5,823,994 A | 10/1998 | Sharkey et al. | 604/60 |
| 5,824,093 A * | 10/1998 | Ray et al. | 623/17 |
| 5,876,404 A | 3/1999 | Zucherman | 606/61 |
| 5,919,235 A | 7/1999 | Husson et al. | 623/17 |
| 5,951,555 A | 9/1999 | Rehak et al. | 606/61 |
| 5,954,716 A | 9/1999 | Sharkey et al. | 606/32 |
| 5,976,186 A * | 11/1999 | Bao et al. | 6223/17 |
| 5,980,504 A | 11/1999 | Sharkey et al. | 604/510 |
| 5,984,925 A | 11/1999 | Apgar | 606/69 |
| 5,989,291 A | 11/1999 | Ralph et al. | 623/17 |
| 6,004,320 A | 12/1999 | Casscells et al. | 606/49 |
| 6,007,533 A | 12/1999 | Casscells et al. | 606/45 |
| 6,007,570 A | 12/1999 | Sharkey et al. | 607/96 |
| 6,022,376 A * | 2/2000 | Assell et al. | 623/17 |
| 6,068,628 A | 5/2000 | Fanton et al. | 606/41 |
| 6,073,051 A | 6/2000 | Sharkey et al. | 607/99 |
| 6,095,149 A | 8/2000 | Sharkey et al. | 128/898 |
| 6,099,514 A | 8/2000 | Sharkey et al. | 604/264 |
| 6,110,210 A * | 8/2000 | Norton et al. | 623/17.16 |
| 6,122,549 A | 9/2000 | Sharkey et al. | 607/99 |
| 6,126,682 A | 10/2000 | Sharkey et al. | 607/96 |
| 6,132,465 A * | 10/2000 | Ray et al. | 623/17.16 |
| 6,135,999 A | 10/2000 | Fanton et al. | 606/96 |
| 6,162,217 A | 12/2000 | Kannenberg et al. | 606/34 |
| 6,168,593 B1 | 1/2001 | Sharkey et al. | 606/34 |
| 6,187,043 B1 * | 2/2001 | Ledergerber | 623/8 |
| 6,224,630 B1 | 5/2001 | Bao et al. | 623/17 |
| 6,231,615 B1 * | 5/2001 | Preissman | 623/23.73 |
| 6,245,107 B1 * | 6/2001 | Ferree | 623/17 |
| 6,264,695 B1 * | 7/2001 | Stoy | 623/17.16 |
| 6,280,475 B1 * | 8/2001 | Bao et al. | 623/17.16 |

FOREIGN PATENT DOCUMENTS

| | | |
|---|---|---|
| WO | WO 99/61084 | 12/1999 |
| WO | WO 00/62832 | 10/2000 |
| WO | WO 01/10316 | 2/2001 |
| WO | WO 01/12107 A1 | 2/2001 |

* cited by examiner

*Primary Examiner*—Jeffrey A. Smith
*Assistant Examiner*—Michael B. Priddy

(57) ABSTRACT

Devices and methods for treating a damaged intervertebral disc to reduce or eliminate associated back pain. Dynamic bias devices and reinforcement devices are disclosed, which may be used individually or in combination, to eliminate nerve impingement associated with the damaged disc, and/or to reinforce the damaged disc, while permitting relative movement of the vertebrae adjacent the damaged disc.

11 Claims, 24 Drawing Sheets

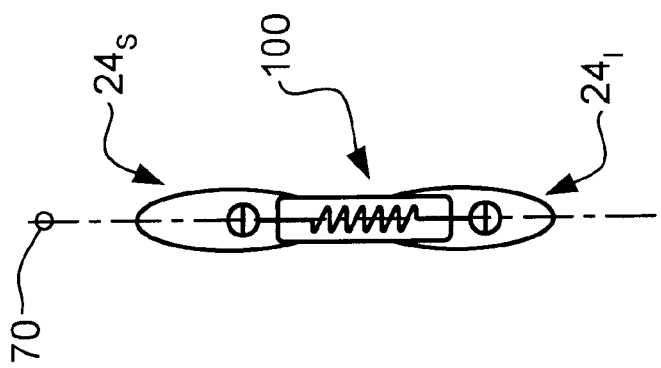
FIG. 5B
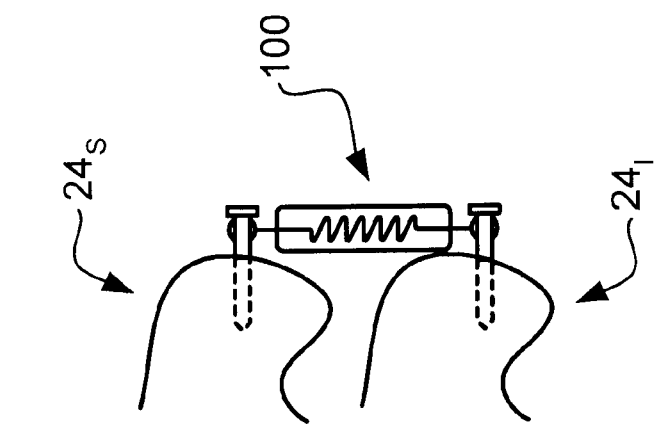
FIG. 5A

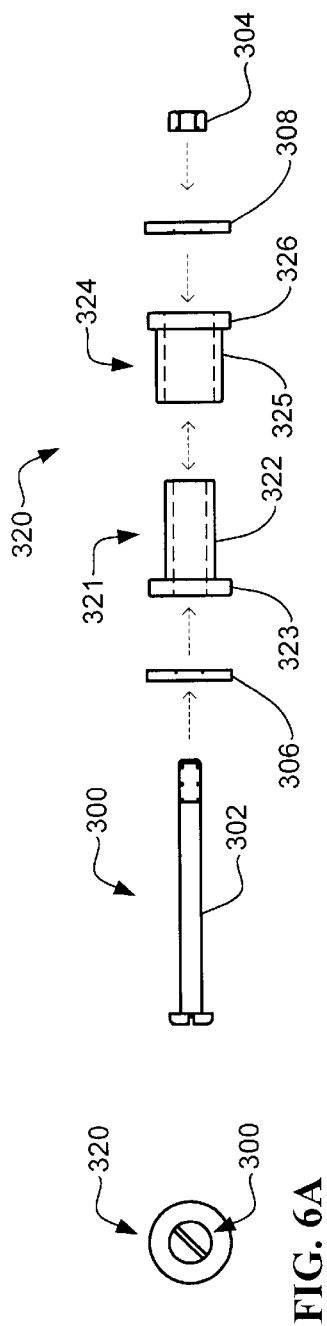

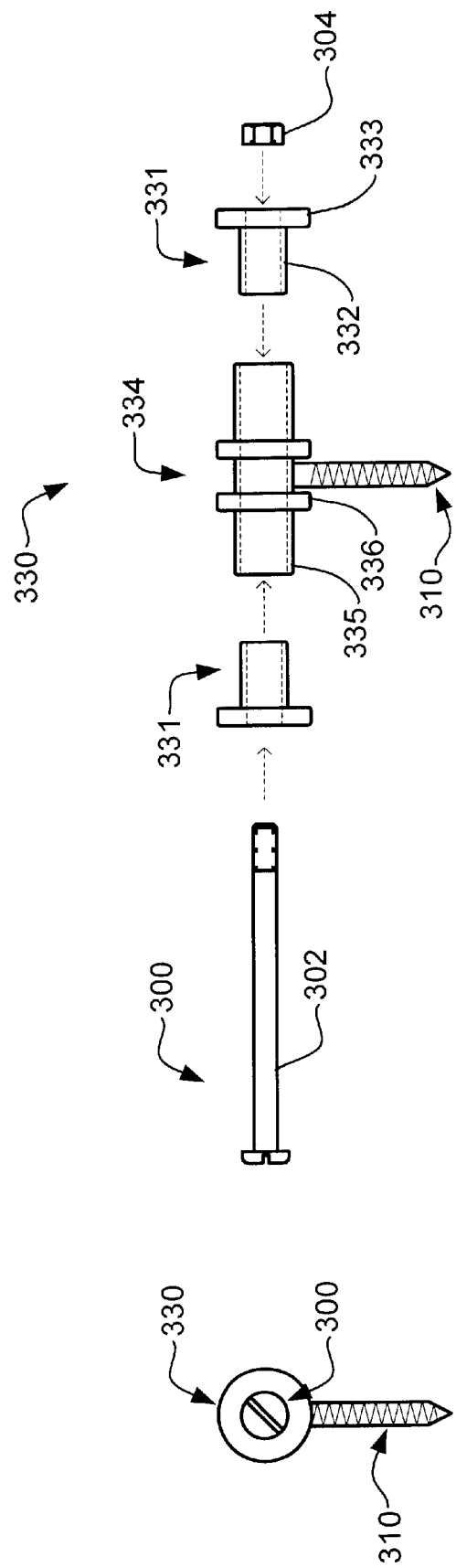

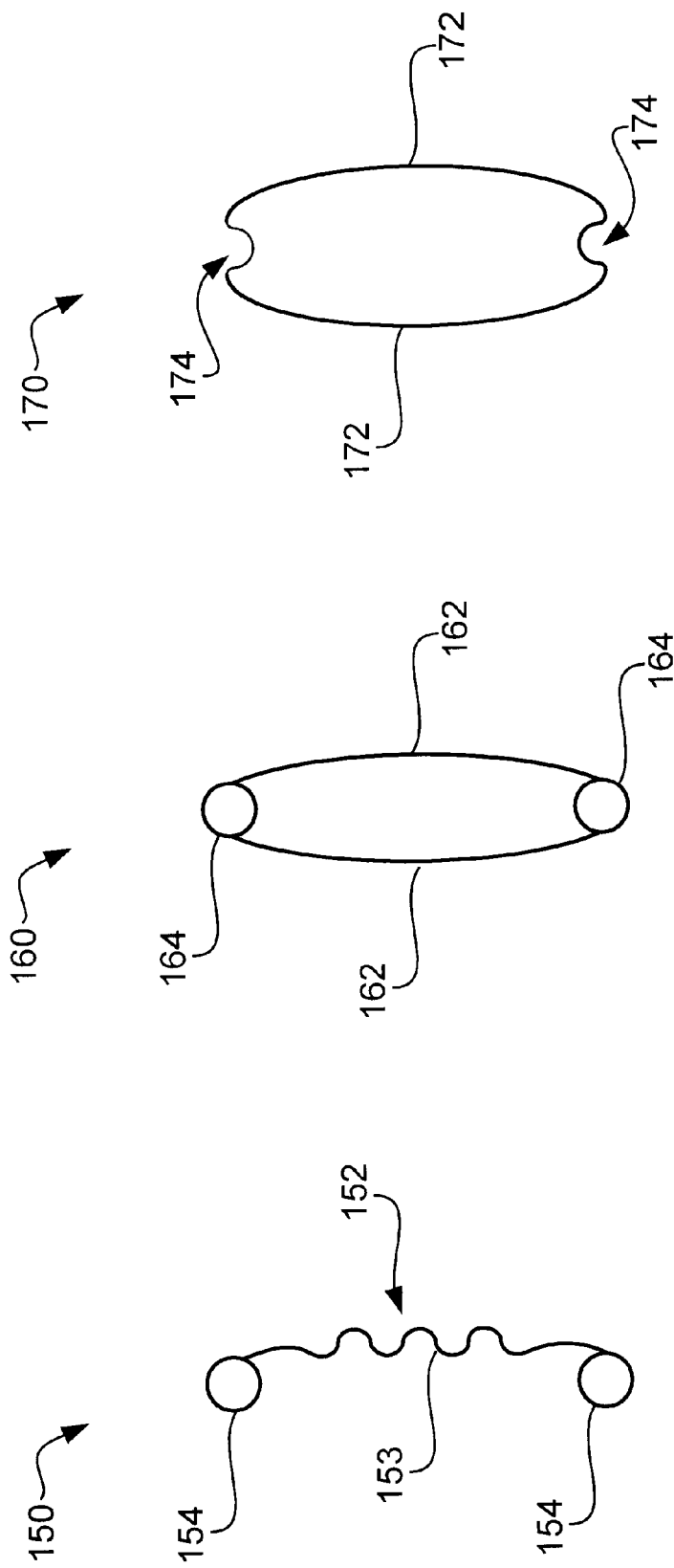

DEVICES AND METHODS FOR THE TREATMENT OF SPINAL DISORDERS

FIELD OF THE INVENTION

The present invention generally relates to spinal implants. Specifically, the present invention relates to implantable devices and methods for the treatment of spinal disorders associated with the intervertebral disc.

BACKGROUND OF THE INVENTION

Back pain is one of the most common and often debilitating conditions affecting millions of people in all walks of life. Today, it is estimated that over ten million people in the United States alone suffer from persistent back pain. Approximately half of those suffering from persistent back pain are afflicted with chronic disabling pain, which seriously compromises a person's quality of life and is the second most common cause of worker absenteeism. Further, the cost of treating chronic back pain is very high, even though the majority of sufferers do not receive treatment due to health risks, limited treatment options and inadequate therapeutic results. Thus, chronic back pain has a significantly adverse effect on a person's quality of life, on industrial productivity, and on heath care expenditures.

Some forms of back pain are not chronic and may be simply treated by rest, posture adjustments and painkillers. For example, some forms of lower back pain (LBP) are very common and may be caused by unusual exertion or injury. Unusual exertion such has heavy lifting or strenuous exercise may result in back strain such as a pulled muscle, sprained muscle, sprained ligament, muscle spasm, or a combination thereof. An injury caused by falling down or a blow to the back may cause bruising. These forms of back pain are typically non-chronic and may be self-treated and cured in a few days or weeks.

Other types of non-chronic back pain may be treated by improvements in physical condition, posture and/or work conditions. For example, being pregnant, obese or otherwise significantly overweight may cause LBP. A mattress that does not provide adequate support may cause back pain in the morning. Working in an environment lacking good ergonomic design may also cause back pain. In these instances, the back pain may be cured by eliminating the culprit cause. Whether it is excess body weight, a bad mattress, or a bad office chair, these forms of back pain are readily treated.

However, some forms of back pain are chronic and are the result of spinal disorders which are not readily treated. Such spinal disorders may cause severe back pain, the origin of which may or may not be certain. A prevalent clinical theory is that pain arises from physical impingement of the nerve roots or the spinal cord. Such nerve impingement may have of a number of different causes, but generally results from either a disc protrusion or from narrowing of the intervertebral foramina which surround the nerve roots. Another clinical theory is that damage to the disc, either from injury, degradation or otherwise, causes physical impingement of the disc nerves, which are primarily disposed about the periphery of the annulus, but may grow into fissures of a damaged disc.

Disc protrusions may be caused by a physical injury to the disc or by natural degradation of the disc such as by degenerative disc disease (DDD). Physical injury may cause damage to the annulus fibrosus which allows a portion of the disc, such as the nucleus pulposus, to protrude from the normal disc space. DDD may cause the entire disc to degenerate to such a degree that the annulus fibrosus bulges outward, delaminates or otherwise separates such that a portion of the disc protrudes from the normal disc space. In either case, the disc protrusion may impinge on a spinal nerve root causing severe pain. Impingement on the nerve root may also be caused by conditions unrelated to the disc such as by a spinal tumor or spinal stenosis (abnormal bone growth), but disc protrusions are the most common cause. Depending on the cause and nature of the disc protrusion, the condition may be referred to as a disc stenosis, a disc bulge, a herniated disc, a slipped disc, a prolapsed disc or, if the protrusion separates from the disc, a sequestered disc.

Nerve root impingement most often occurs in the lumbar region of the spinal column since the lumbar discs bear significant vertical loads relative to discs in other regions of the spine. In addition, disc protrusions in the lumbar region typically occur posteriorly because the annulus fibrosus is thinner on the posterior side than on the anterior side and because normal posture places more compression on the posterior side. Posterior protrusions are particularly problematic since the nerve roots are posteriorly positioned relative to the intervertebral discs. When a posterior disc protrusion presses against a nerve root, the pain is often severe and radiating, and may be aggravated by such subtle movements as coughing, bending over, or remaining in a sitting position for an extended period of time.

A common treatment for disc protrusion is discectomy, which is a procedure wherein the protruding portion of the disc is surgically removed. However, discectomy procedures have an inherent risk since the portion of the disc to be removed is immediately adjacent the nerve root and any damage to the nerve root is clearly undesirable. Furthermore, discectomy procedures are not always successful long term because scar tissue may form and/or additional disc material may subsequently protrude from the disc space as the disc deteriorates further. The recurrence of a disc protrusion may necessitate a repeat discectomy procedure, along with its inherent clinical risks and less than perfect long term success rate. Thus, a discectomy procedure, at least as a stand-alone procedure, is clearly not an optimal solution.

Discectomy is also not a viable solution for DDD when no disc protrusion is involved. As mentioned above, DDD causes the entire disc to degenerate, narrowing of the intervertebral space, and shifting of the load to the facet joints. If the facet joints carry a substantial load, the joints may degrade over time and be a different cause of back pain. Furthermore, the narrowed disc space can result in the intervertebral foramina surrounding the nerve roots to directly impinge on one or more nerve roots. Such nerve impingement is very painful and cannot be corrected by a discectomy procedure.

As a result, spinal fusion, particularly with the assistance of interbody fusion cages, has become a preferred secondary procedure, and in some instances, a preferred primary procedure. Spinal fusion involves permanently fusing or fixing adjacent vertebrae. Hardware in the form of bars, plates, screws and cages may be utilized in combination with bone graft material to fuse adjacent vertebrae. Spinal fusion may be performed as a stand-alone procedure or may be performed in combination with a discectomy procedure. By placing the adjacent vertebrae in their nominal position and fixing them in place, relative movement therebetween may be significantly reduced and the disc space may be restored to its normal condition. Thus, theoretically, aggravation caused by relative movement between adjacent vertebrae (and thus impingement on the nerve root by a disc protrusion and/or impingement from bone may be reduced if not eliminated.

However, the success rate of spinal fusion procedures is certainly less than perfect for a number of different reasons, none of which are well understood. In addition, even if spinal fusion procedures are initially successful, they may cause accelerated degeneration of adjacent discs since the adjacent discs must accommodate a greater degree of motion. The degeneration of adjacent discs simply leads to the same problem at a different anatomical location, which is clearly not an optimal solution. Furthermore, spinal fusion procedures are invasive to the disc, risk nerve damage and, depending on the procedural approach, either technically complicated (endoscopic anterior approach), invasive to the bowel (surgical anterior approach), or invasive to the musculature of the back (surgical posterior approach).

Another procedure that has been less than clinically successful is total disc replacement with a prosthetic disc. This procedure is also very invasive to the disc and, depending on the procedural approach, either invasive to the bowel (surgical anterior approach) or invasive to the musculature of the back (surgical posterior approach). In addition, the procedure may actually complicate matters by creating instability in the spine, and the long term mechanical reliability of prosthetic discs has yet to be demonstrated.

Many other medical procedures have been proposed to solve the problems associated with disc protrusions. However, many of the proposed procedures have not been clinically proven and some of the allegedly beneficial procedures have controversial clinical data. From the foregoing, it should be apparent that there is a substantial need for improvements in the treatment of spinal disorders, particularly in the treatment of nerve impingement as the result of damage to the disc, whether by injury, degradation, or the like.

SUMMARY OF THE INVENTION

The present invention addresses this need by providing improved devices and methods for the treatment of spinal disorders. As used herein, the term spinal disorder generally refers to a degradation in spinal condition as the result of injury, aging or the like, as opposed to a spinal deformity resulting from growth defects. The improved devices and methods of the present invention specifically address nerve impingement as the result of damage to the disc, particularly in the lumbar region, but may have other significant applications not specifically mentioned herein. For purposes of illustration only, and without limitation, the present invention is discussed in detail with reference to the treatment of damaged discs in the lumbar region of the adult human spinal column.

As will become apparent from the following description, the improved devices and methods of the present invention reduce if not eliminate back pain while maintaining near normal anatomical motion. Specifically, the present invention provides dynamic bias devices and reinforcement devices, which may be used individually or in combination, to eliminate nerve impingement associated with a damaged disc, and/or to reinforce a damaged disc, while permitting relative movement of the vertebrae adjacent the damaged disc. The devices of the present invention are particularly well suited for minimally invasive methods of implantation.

The dynamic bias devices of the present invention basically apply a bias force to adjacent vertebrae on either side of a damaged disc, while permitting relative movement of the vertebrae. By applying a bias force, disc height may be restored, thereby reducing nerve impingement. Specifically, by restoring disc height, the dynamic bias devices of the present invention: retract disc protrusions into the normal disc space thereby reducing nerve impingement by the protrusions; reduce the load carried by the facet joints thereby eliminating nerve impingement originating at the joint; restore intervertebral spacing thereby eliminating nerve impingement by the intervertebral foramina; and reduce pressure on portions of the annulus thereby alleviating nerve impingement in disc fissures.

The reinforcement devices of the present invention basically reinforce a damaged disc, restore disc height and/or bear some or all of the load normally carried by a healthy disc, thereby reducing nerve impingement. Some embodiments of the reinforcement members of the present invention have a relatively small profile when implanted, but are very rigid, and thus serve to reinforce the disc, particularly the annulus. By reinforcing the disc, and particularly the annulus, disc protrusions may reduced or prevented, thereby eliminating nerve impingement by the protrusions. Other embodiments have a relatively large profile when implanted, and thus serve to increase disc height and/or to bear load. By increasing disc height, the advantages discussed previously may be obtained. By bearing some of the load normally carried by a healthy disc, the load may be redistributed as needed, such as when a dynamic bias device is used.

BRIEF DESCRIPTION OF THE DRAWINGS

FIGS. 5A–5B schematically illustrate left lateral and posterior views, respectively, of a dynamic bias device of the present invention mounted to adjacent vertebrae in the median plane;

FIGS. 6A–6B illustrate end and exploded views, respectively, of a bushing in accordance with a first embodiment of the present invention;

FIG. 6C illustrates a posterior view of the bushing shown in FIGS. 6A–6B mounted to a spinous process;

FIG. 6D illustrates a posterior view of the spinous process shown in FIG. 6C, detailing the counter-bore;

FIGS. 7A–7B illustrate end and exploded views, respectively, of a bushing in accordance with a second embodiment of the present invention;

FIG. 13A illustrates a side view of a dynamic bias device in accordance with a fifth embodiment of the present invention;

FIG. 13B illustrates a side or rear view of a dynamic bias device in accordance with a sixth embodiment of the present invention;

FIG. 13C illustrates a rear view of a dynamic bias device in accordance with a seventh embodiment of the present invention;

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

Figures 1A, 1B:
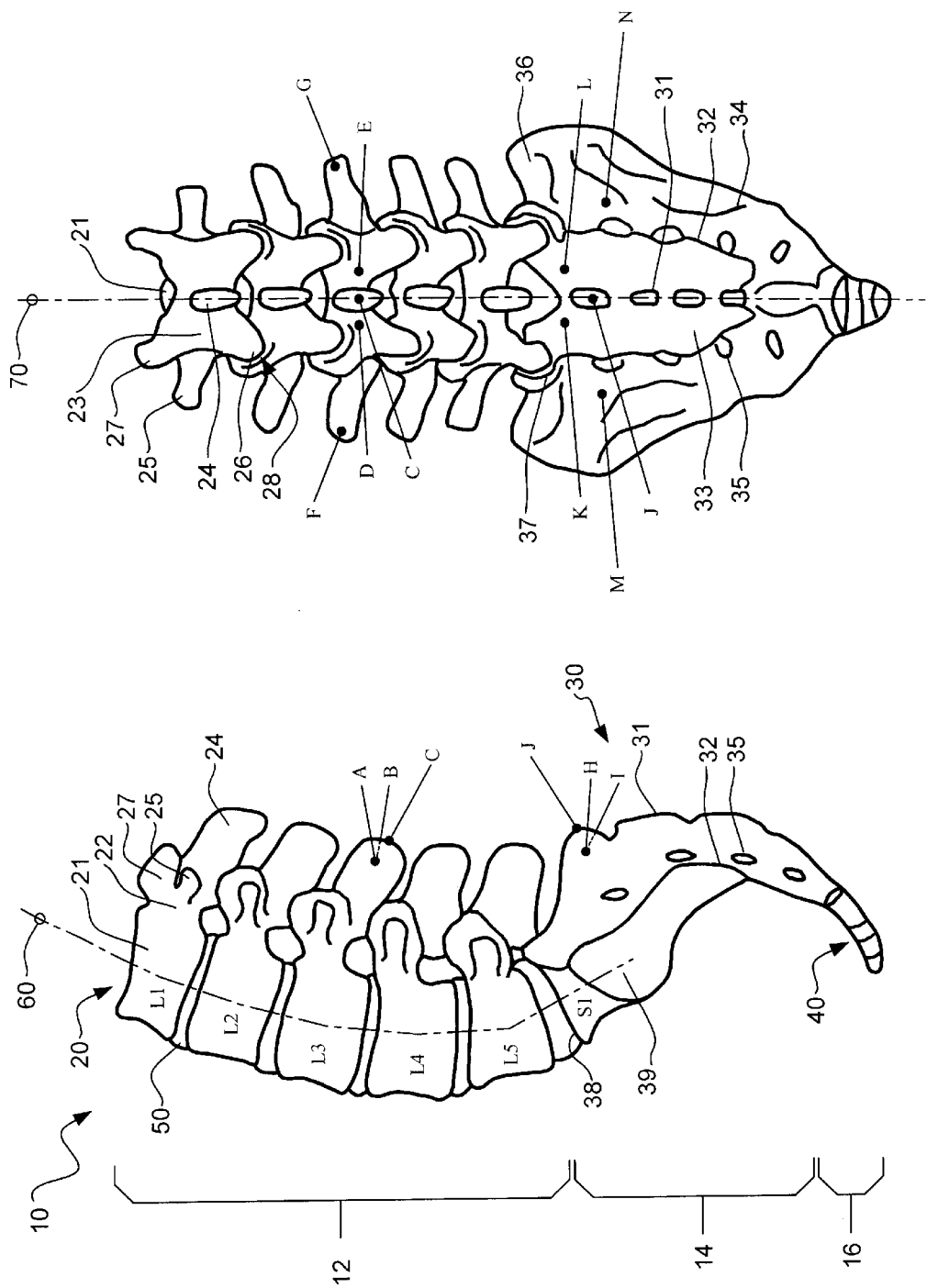
FIGS. 1A and 1B illustrate left lateral and posterior views, respectively, of a portion of the adult human vertebral (spinal) column.

With reference to FIGS. 1A and 1B, the lower portion of an adult human vertebral column 10 is illustrated in left lateral and posterior views, respectively. The upper portion of the vertebral column 10 includes the thoracic region and the cervical region, which are not shown for purposes of simplified illustration only. The lower portion of the vertebral column 10 includes the lumbar region 12, the sacrum 14 and the coccyx 16. The sacrum 14 and the coccyx 16 are sometimes collectively referred to as the pelvic curvature.

The vertebral column 10 includes an axis of curvature 60 which generally forms a double-S shape when viewed laterally. The vertebral column 10 also includes a median plane 70 which is a sagittal plane bisecting the vertebral column 10 into symmetrical left lateral and right lateral portions. In posterior views, the median plane 70 appears as a line.

The lumbar region 12 of the vertebral column 10 includes five (5) vertebrae 20 (labeled L1, L2, L3, L4 and L5) separated by intervertebral discs 50. The sacrum 14, which includes five (5) fused vertebrae 30 (superior vertebra 30 labeled S1), is separated by a single disc 50 from the coccyx 16, which includes four (4) fused vertebrae 40. Although not labeled, the intervertebral discs 50 may be referenced by their respective adjacent vertebrae. For example, the disc 50 between the L4 and L5 lumbar vertebrae 20 may be referred to as the L4L5 disc. Similarly, the disc 50 between the L5 lumbar vertebra 20 and the S1 sacral vertebra 30 may be referred to as the L5S1 disc.

Although each vertebra 20/30/40 is a unique and irregular bone structure, the vertebrae 20 of the lumbar region 12 (in addition to the thoracic and cervical regions) have common structures. Each vertebra 20 of the lumbar region 12 generally includes a body portion 21 and a vertebral arch portion 22/23 which encloses the vertebral foramen (not visible) in which the spinal cord is disposed. The vertebral arch 22/23 includes two pedicles 22 and two laminae 23. A spinous process 24 extends posteriorly from the juncture of the two laminae 23, and two transverse processes 25 extend laterally from each laminar 23. Four articular processes 26/27 extend inferiorly 26 and superiorly 27 from the laminae 23. The inferior articular process 26 rests in the superior articular process 27 of the adjacent vertebra to form a facet joint 28.

The five (5) vertebrae 30 of the sacrum 14 are fused together to form a single rigid structure. The sacrum 14 includes a median sacral crest 31 which roughly corresponds to the spinous processes of the vertebrae 30, and two intermediate sacral crests 32 which roughly correspond to the articular processes of the vertebrae 30. The sacral laminae 33 are disposed between the median 31 and intermediate 32 sacral crests. Two lateral sacral crests 34 are disposed on either side of the sacral foraminae 35. The sacrum 14 also includes a pair of sacral wings 36 which define auricular surfaces 39. The superior (S1) sacral vertebra 30 includes two superior articular processes 37 which engage the inferior articular processes 26 of the L5 lumber vertebra 20 to form a facet joint, and the base 38 of the superior sacral vertebra S1 is joined to the L5S1 disc 50.

Figure 15B:
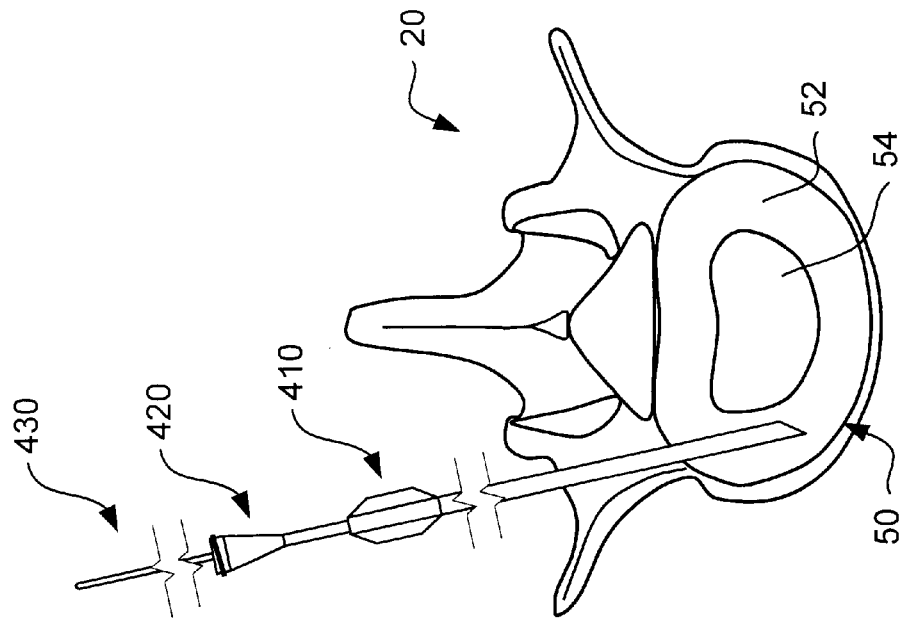
FIGS. 15A–15J illustrate steps for implanting a self-expanding reinforcement member.
Figure 15A:
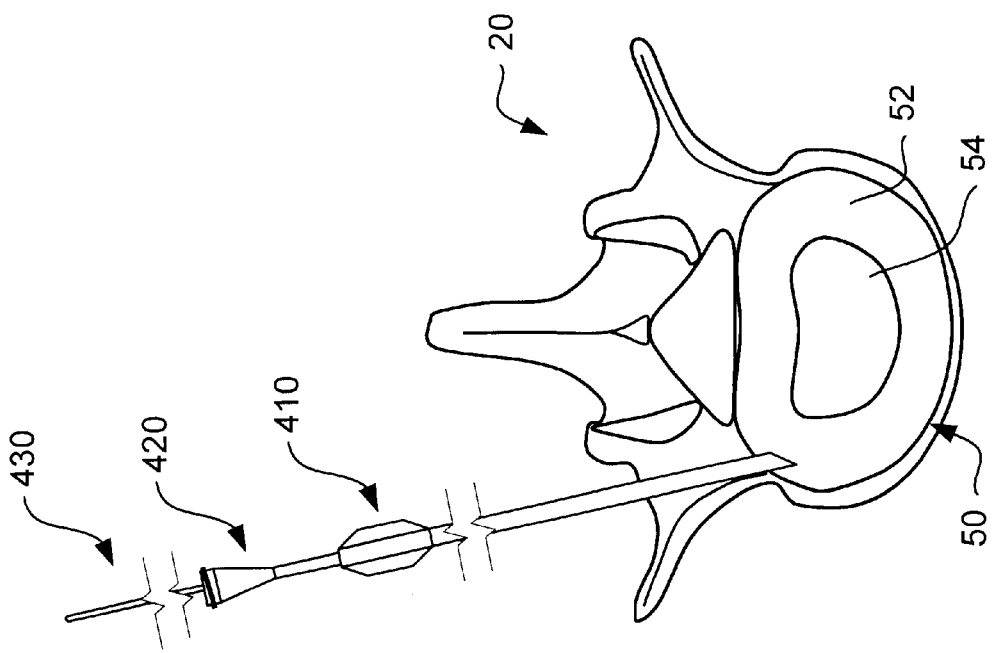

Each intervertebral disc 50 includes an annulus fibrosus 52 surrounding a nucleus pulposus 54, which are more clearly visible in FIG. 15A. The posterior annulus 52 is generally thinner than the anterior annulus 52, which may account for the higher incidence of posterior disc protrusions. As used herein, a disc protrusion generically refers to any portion of the disc that protrudes from the normal disc space. Common clinical conditions that may be characterized as a disc protrusion include a disc stenosis, a disc bulge, a herniated or sequestered disc, a slipped disc, and a prolapsed disc. Generally, a disc protrusion results in a decrease in disc height proportional to the volume of the protrusion. A degenerative disc may sometimes only involve the loss of disc height, and may or may not involve any significant protrusion. However, both degenerative discs and a disc protrusions usually involve some loss in disc height.

A common theory is that each intervertebral disc 50 forms one support point and the facet joints form two support points of what may be characterized as a three point support structure between adjacent vertebrae. However, in the lumbar region 12, the facet joints 28 are substantially vertical, leaving the disc 50 to carry the vast majority of the load. As between the annulus fibrosus 52 and the nucleus pulposus 54 of the disc 50, it is commonly believed that the nucleus 54 bears the majority of the load. This belief is based on the theory that the disc 50 behaves much like a balloon or tire, wherein the annulus 22 merely serves to contain the pressurized nucleus 54, and the nucleus 54 bears all the load.

However, this theory is questionable since the annulus fibrosus 52 comprises 60% of the total disc 50 cross-section, and the nucleus pulposus 54 only comprises 40% of the total disc 50 cross-section. In addition, the annulus fibrosus 52 is made of 40–60% organized collagen in the form of a laminated structure, whereas the nucleus pulposus 54 is made of 18–30% collagen in the form of a relatively homogenous gel. It seems a more plausible theory is that the annulus fibrosus 52 is the primary load bearing portion of the disc 50.

Figure 2B:
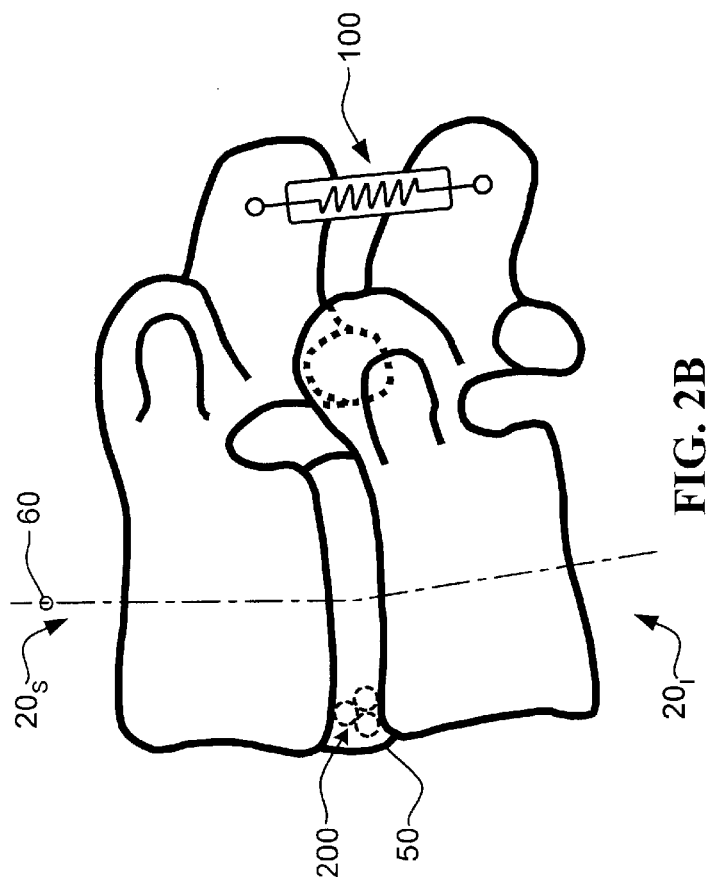
FIG. 2B illustrates a left lateral view of an intervertebral disc disposed between adjacent vertebrae as in FIG. 2A, wherein dynamic bias devices and reinforcement devices of the present invention, which are illustrated schematically, restore normal disc height and eliminate the disc protrusion.
Figure 2A:
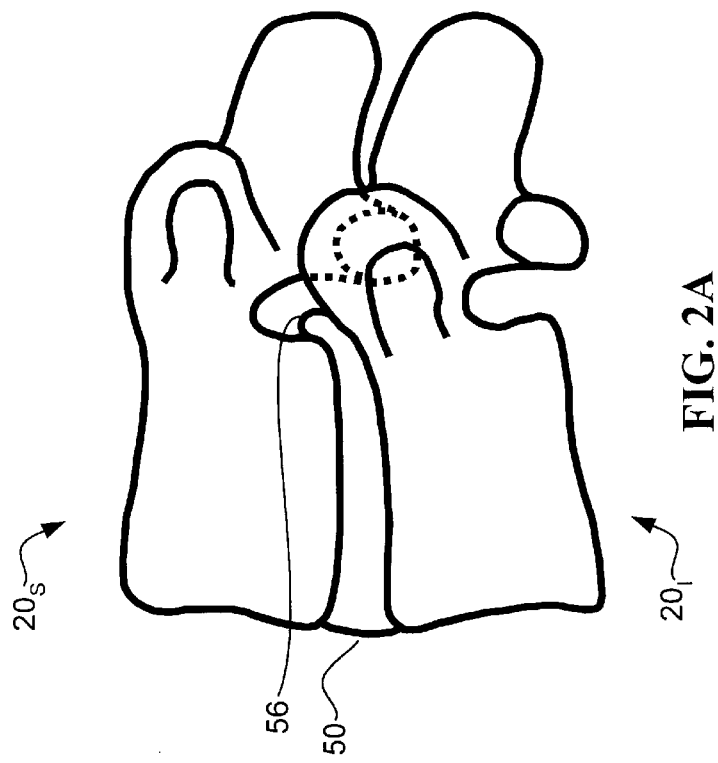
FIG. 2A illustrates a left lateral view of an intervertebral disc disposed between adjacent vertebrae, wherein the disc is partially protruding from the normal disc space and the disc height is reduced.

With reference to FIG. 2A, a left lateral view of an intervertebral disc 50 disposed between adjacent vertebrae $20_S$ (superior) and $20_I$ (inferior) is illustrated, wherein the disc 50 is partially protruding 56 from the normal disc space and the disc height is reduced. Although the disc 50 is shown to include a protrusion 56, the reduction in disc height may or may not be accompanied with a protrusion 56 as discussed previously. For example, if the disc 50 is degenerated, the disc height may be reduced with or without a corresponding protrusion 56.

It should be understood that the vertebrae shown in FIGS. 2A and 2B generically refer to any two adjacent vertebrae or any series of adjacent vertebrae, and that lumbar vertebrae $20_s$ and $20_I$ are specifically shown for purposes of illustration only. This generic method of illustrating vertebrae also applies to the remainder of the Figures.

With reference to FIG. 2B, a left lateral view of the intervertebral disc 50 disposed between adjacent vertebrae $20_S$ and $20_I$ is illustrated as in FIG. 2A. However, in this Figure, devices 100 and 200 of the present invention, which are illustrated schematically, eliminate the disc protrusion 56 and restore normal disc height. Specifically, one or more dynamic bias devices 100 and one or more reinforcement members 200 are utilized, either in combination or individually.

The dynamic bias device 100 restores disc height and, by conservation of disc volume, retracts the protrusion into the normal disc space thereby reducing nerve impingement by the protrusion. Restoring disc height also reduces the load carried by the facet joints thereby eliminating nerve impingement originating at the joint, restores intervertebral spacing thereby eliminating nerve impingement by the intervertebral foramina, and reduces pressure on portions of the annulus thereby alleviating nerve impingement in disc fissures.

The dynamic bias device 100 basically applies a bias force to the adjacent vertebrae $20_S$ and $20_I$ to which it is connected, but allows relative movement of the vertebrae $20_S$ and $20_I$. The dynamic bias device 100 is conceptually similar to a spring attached to the adjacent vertebrae $20_S$ and $20_I$. The dynamic bias device 100 applies a bias force (usually repulsive) between the vertebrae $20_S$ and $20_I$ when the disc height is normal or less than normal. The bias force is preferably set such that the disc height is normal with normal posture and loading, and increases with posterior flexure and/or added vertical load. The details of the design and use of the dynamic bias device 100 will be discussed in greater detail hereinafter, particularly with reference to FIGS. 3A–3C, 4A–4B, 5A–5B, 10A–10C, 11A–11B, 12A–12C, and 13A–13C.

Because most protrusions 56 are posterior, the dynamic bias device 100 is preferably mounted posterior to the axis of curvature 60. Locating the dynamic bias device 100 posterior to the axis of curvature 60 shifts the load carried by the disc 50 from the posterior portion of the disc to the anterior portion of the disc 50. Locating the dynamic bias device 100 posterior to the axis of curvature 60 also reduces the load carried by the facet joints. Preferably, the dynamic bias device 100 applies a substantially vertical bias force, with the direction independent of displacement.

Because more load will be shifted to the anterior portion of the disc 50 with a posterior mounted dynamic bias device 100, reinforcement members 200 may be placed in the anterior annulus 52, to effectively bolster the anterior portion of the disc. The reinforcement members 200 may be used to reinforce the disc, restore disc height and/or bear the load normally carried by annulus. The reinforcement members 200 are relatively rigid and thus serve to reinforce the disc 50 where inserted. In addition, the reinforcement members 200 may have a relatively large profile when implanted and thus increase disc height. The reinforcement members 200 are particularly beneficial if the disc 50 is degenerated, or if the disc 50 will likely become degenerated with the change in load distribution. The details of the design and use of the reinforcement members 200 will be discussed in greater detail hereinafter, particularly with reference to FIGS. 14A–14D and 15A–15R.

As mentioned previously, one or more dynamic bias devices 100 and one or more reinforcement members 200 may be utilized, either alone or in combination. Specifically: one or more dynamic bias devices 100 may be used alone; one or more spacer devices 200 may be used alone; and one or more dynamic bias devices 100 and one or more reinforcement members 200 may be used in combination. If a combination of devices 100/200 is used, it is believed that the use of one or more posterior dynamic bias devices 100 in combination with one or more anterior reinforcement members 200 is most effective in treating posterior protrusions 56, facet joint degradation, and nerve impingement by intervertebral foraminae, which are believed to be the most common culprits of chronic LBP.

As an alternative to the arrangement shown in FIG. 2B, two or more dynamic bias devices 100 may be attached to the vertebrae on opposite sides of vertebrae $20_S$ and $20_I$. Specifically, one or more dynamic bias devices 100 is connected to vertebra $20_S$ and the vertebra immediately superior to vertebra $20_S$, and one or more dynamic bias devices 100 is connected to vertebra $20_I$ and the vertebra immediately inferior to vertebra $20_I$. With this arrangement, the dynamic bias devices 100 are primarily applying a traction force to effectively pull vertebrae $20_S$ and $20_I$ apart, thereby eliminating the disc protrusion 56 and restoring normal disc height.

Figure 3C:
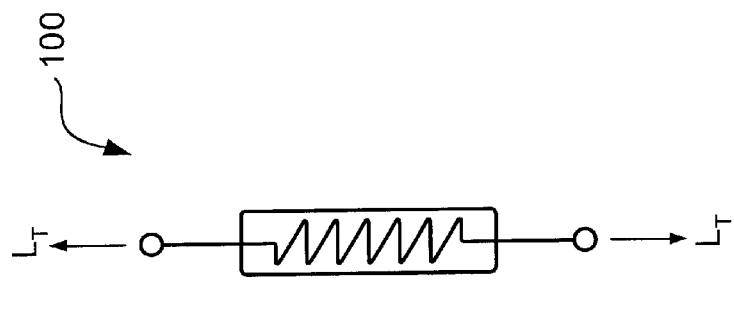
FIGS. 3A–3C schematically illustrate a dynamic bias device 100 in accordance with the present invention.
Figure 3B:
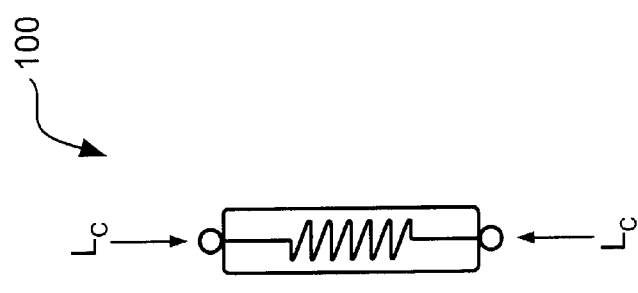
Figure 3A:
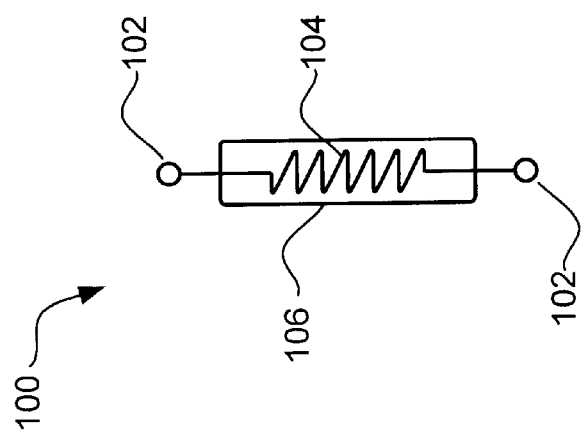

With reference to FIGS. 3A–3C, the dynamic bias device 100 is schematically illustrated under conditions of no-load, compression load ($L_C$), and traction load ($L_T$), respectively. The dynamic bias device 100 includes a pair of attachment members 102, a bias member 104, and a housing 106. Attachment members 102 facilitate attachment of the dynamic bias device 100 to vertebrae $20_S$ and $20_I$, as shown in FIG. 2B. Bias member 104 functions to apply a bias force between the attachment members 102. Housing 106 functions to separate the moving portions of dynamic bias device 100 from the surrounding muscle, ligaments and other tissue when the dynamic bias device 100 is implanted.

Attachment members 102 may comprise a wide variety of mechanical connection designs, and may incorporate into their design, or be used in combination with, other machine elements not specifically mentioned herein. For purposes of illustration only, the each attachment member 102 is shown as loop which may be connected to the vertebrae by fasteners and bushings, specific examples of which are described in detail with reference to FIGS. 6A–6D, 7A–7B, 8A–8B and 9A–9B. These specific examples are provided by way of example, not limitation. Those skilled in the art will recognize that the attachment members 102 may comprise or include screws, rivets, spikes, keys, pins, cotters, splines, couplings, bushings, washers, and the like, without departing from the scope or spirit of the present invention.

The primary function of the attachment members 102 is to fixedly secure the ends of the bias member 104 to the vertebrae $20_S$ and $20_I$. Preferably, the attachment members 102 are secured to the vertebrae $20_S$ and $20_I$ such that translational movement is minimized or eliminated, and such that rotational movement is permitted between each attachment member 102 and each vertebrae $20_S$ and $20_I$. Providing attachment members 102 with these fictional attributes permits the dynamic bias device 100 to effectively transmit a bias force to each vertebrae $20_S$ and $20_I$, allow relative movement therebetween, and minimize stress on the vertebrae $20_S$ and $20_I$ at the attachment points.

Bias member 104 functions to apply a bias force, either attraction or repulsion, between the attachment members 102. The bias force generally increases or decreases with displacement of the ends of the bias member 104, as with a conventional spring. In addition, the bias force may increase or decrease with the time derivative of displacement (i.e., velocity) of the ends of the bias member 104, as with a conventional damper or shock absorber. As shown in FIG. 3B, the bias member 104 compresses in response to a compression load ($L_C$), thereby increasing or decreasing the bias force. Similarly, as shown in FIG. 3C, the bias member 104 extends in response to a traction load ($L_T$), thereby increasing or decreasing the bias force.

If the dynamic bias devices 100 are attached to vertebrae $20_S$ and $20_I$ (compression embodiment), as shown in FIG. 2B, the bias force of the bias member 104 increases in response to a compression load ($L_C$), and decreases in response to a traction load ($L_T$). In addition, the bias member 104 normally operates in compression. Preferably, the bias force of the bias member 104 is adjusted such that the disc is restored to a more normal height when the dynamic bias device 100 is implanted. Because the disc height is usually initially less than normal, the dynamic bias device 100 is attached to the vertebrae with the bias member 104 preloaded in compression or with the vertebrae $20_S$ and $20_I$ in traction or otherwise spread apart. In this manner, for a given posture, the disc height will be larger following implantation of the dynamic bias device 100 than prior to implantation.

If the dynamic bias devices 100 are attached to the vertebrae on opposite sides of vertebrae $20_S$ and $20_I$ (traction embodiment), as discussed as an alternative to the arrangement shown in FIG. 2B, the bias force of the bias member 104 decreases in response to a compression load ($L_C$), and increases in response to a traction load ($L_T$). With this latter arrangement, the bias member 104 normally operates in tension. Because the bias member 104 normally operates in tension with this arrangement, the bias member 104 may simply comprise a member that is rigid or semi-rigid in tension, such as a cable. Also with this arrangement, the bias force of the bias member 104 is adjusted such that the disc is restored to a more normal height when the dynamic bias device 100 is implanted. Further with this arrangement, because the disc height is usually initially less than normal, the dynamic bias device 100 is attached to the vertebrae with the bias member 104 preloaded in tension or with the vertebrae $20_S$ and $20_I$ in traction or otherwise spread apart.

With either arrangement, the dynamic bias device 100 preferably operates with substantially linear displacement substantially parallel to the axis of curvature 60. However, the amount of displacement will be evenly shared between the dynamic bias devices 100 in the traction embodiment, whereas the compression embodiment requires the fall displacement to be assumed by each dynamic bias device 100. The following ranges of displacement are given with reference to the compression embodiment. When mounted near the posterior portion of adjacent spinous processes, the dynamic bias device 100 may have a total (i.e., maximum) displacement preferably in the range of 1.0 to 3.0 cm to accommodate full posterior to anterior flexure in the L5–S1 region, 0.5 to 1.5 cm to accommodate full posterior to anterior flexure in the L4–L5 region, and 0.25 to 1.0 cm to accommodate full posterior to anterior flexure in the L1–L4 region.

Within these ranges of displacement, it is preferable that bias member 104 operate within its elastic limit, as dictated by the chosen material and geometry of the bias member 104. In addition, because the bias member preferably should be able to withstand 1.0 to 10 million fatigue cycles, it is preferable that bias member 104 operate within its fatigue limit, as dictated by the chosen material and geometry, for the full range of displacement.

As mentioned previously, the bias force may generally increase or decrease with displacement of the ends of the bias member 104, as with a conventional spring. In this situation, the bias force ($F_B$) is generally governed by Hooke's Law where $F_B = K\Delta X$, wherein $F_B$ is linearly proportional to the displacement ($\Delta X$) as dictated by the spring constant (K) of the bias member 104. Also as mentioned previously, the bias force may increase or decrease with the time derivative of displacement (i.e., velocity) of the ends of the bias member 104, as with a conventional damper or shock absorber. In this situation, the bias force ($F_B$) is generally linearly proportional to the derivative of displacement ($\Delta X/\Delta T$) as dictated by the damper constant (P) of the bias member 104. Preferably, the bias force $F_B$ of the bias member 104 is adjusted such that the disc is restored to a more normal height when the dynamic bias device 100 is implanted. The bias force $F_B$ may be adjusted by selecting the spring constant (K) and/or damper constant (P) of the bias member 104 and by pre-loading (compressing) the bias member 104 an initial displacement $\Delta X_i$.

The necessary bias force $F_B$ may be roughly calculated as a function of body weight (BW), the distance of the mounted dynamic bias device 100 from the axis of curvature 60, and the mechanical properties of the surrounding tissues (muscle tissue, connective tissue, joints). The normal net load carried by the lumbar region 12 is roughly 30% BW when laying down, 140% BW when standing, 185% BW when sitting, 215% BW when bending forward, and 250% BW when slouching.

Figure 16:
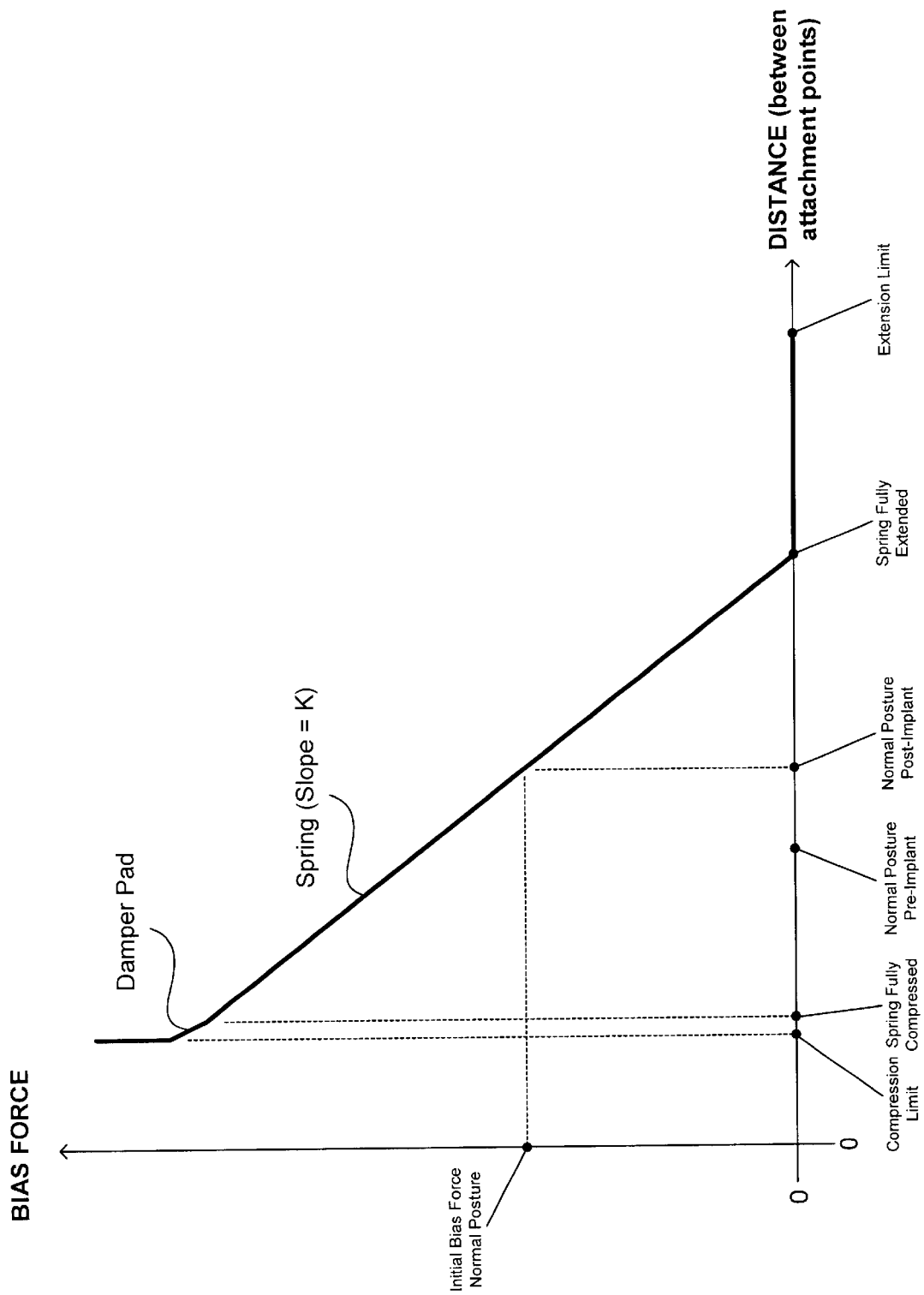
FIG. 16 illustrates a bias force v. displacement curve for the dynamic bias device.

With reference to FIG. 16, a bias force versus attachment point displacement curve for the dynamic bias device 100 is shown. The bias force is intended to be sufficiently high to spread the attachment points (e.g., processes of adjacent vertebrae) and restore normal disc height in all postures. For example, in normal standing posture, the bias force is sufficiently high to spread the attachment points as shown in FIG. 16, such that more normal disc size and shape is obtained. As the spine is placed in flexion and extension, the amount of force carried by the dynamic bias device 100 will change as a function of the spring properties, including the spring constant (K) and the compression length of the spring.

In a preferred embodiment, the bias force is sufficient to shift the pre-implant (normal posture) distance to the post-implant (normal posture) distance. To prevent excessive compression of the disc, particularly the posterior disc, it is also preferred that the bias force increase significantly as the attachment points come closer, as by extension, lifting and/or poor posture. This is facilitated by the natural increase in bias force of the spring as the distance decreases, and is aided by the damper pad and the compression limit (bottomed out) of the spring. In addition, because the dynamic bias device is intended to limit excessive compression of the posterior disc, and not necessarily intended to limit flexion of the spine, it is also preferable that the bias force approach zero (spring fully extended) at a distance which is less than the extension limit of the dynamic bias device.

Thus, by way of example, not limitation, the bias force may be in the range of 1% to 30% BW when laying down. With other postures after implantation, the bias force may be estimated by subtracting the contribution of body weight from the load carried by lumbar region 12, which is approximately 50% BW (head=5% BW; arms=9% BW; trunk=36% BW). As such, the bias force may be in the range of 10% to 90% BW when standing.

Figure 4B:
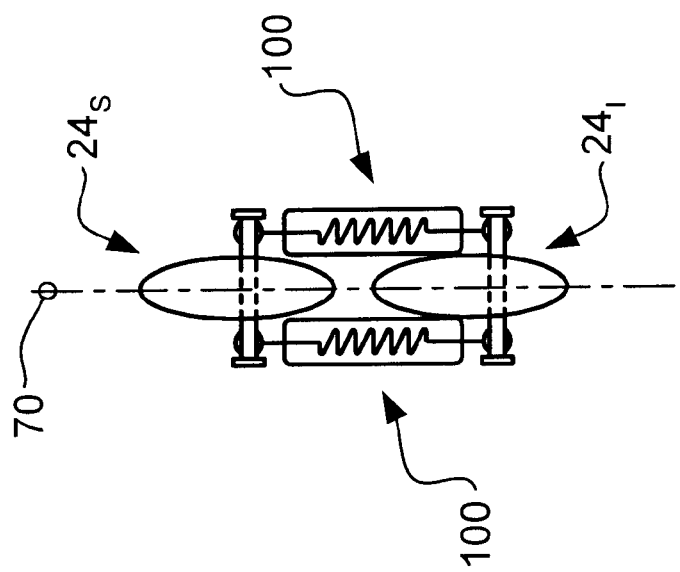
FIGS. 4A–4B schematically illustrate left lateral and posterior views, respectively, of dynamic bias devices of the present invention mounted to adjacent vertebrae equidistant from the median plane.
Figure 4A:
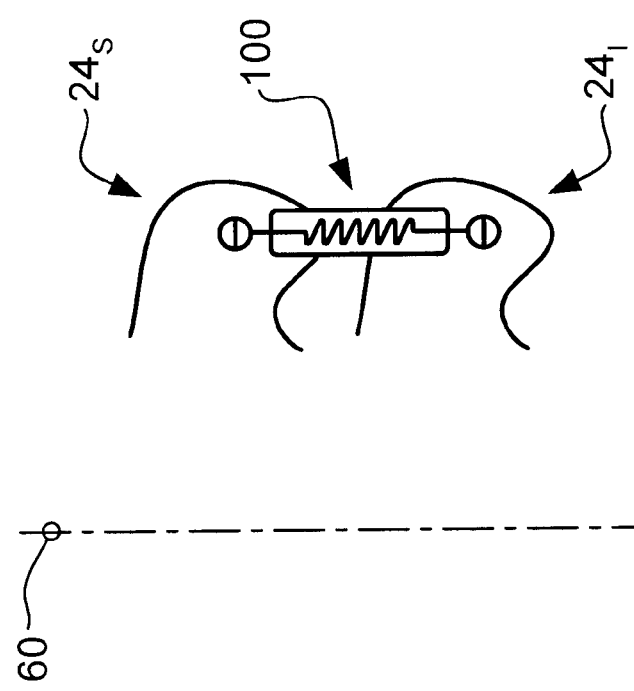

With reference to FIGS. 4A–4B and 5A–5B, left lateral and posterior views of dynamic bias devices 100 are schematically illustrated as being mounted to adjacent spinous processes $24_S$ and $24_I$ of adjacent vertebrae $20_S$ and $20_I$. When two or more dynamic bias devices 100 are utilized per pair of vertebrae as shown in FIGS. 4A and 4B, the dynamic bias devices 100 are preferably mounted substantially equidistant from the median plane 70, or otherwise symmetric about the median plane 70, in order to avoid causing lateral bias or curvature of the spine 10. Note that the dynamic bias devices 100 may be mounted substantially vertical as shown or at an angle to the median plane 70 and satisfy these criteria. When only one dynamic bias device 100 is utilized per pair of vertebrae as shown in FIG. 5A and 5B, the dynamic bias device 100 is preferably mounted in or near the median plane 70 for the same reason.

Although it is preferable to have the dynamic bias device(s) 100 near the median plane 70, substantially equidistant from the median plane 70, or otherwise symmetric about the median plane 70, it is possible to have multiple dynamic bias devices 100 mounted asymmetrically while maintaining balanced bias forces about the median plane 70. The objective is to avoid causing lateral bias or curvature of the spine 10, which is a function of balancing bias forces and moments about the median plane 70.

The bias forces are vectors which have a magnitude governed by the properties of the bias member 104, and a direction dictated by the mounting position of the dynamic bias device 100. Each dynamic bias device 100 has two bias force vectors, one for each attachment member 102 at each attachment point. Each bias force vector has a moment arm equal to the distance from the attachment point to the median plane 70. For each attachment point, the product of the moment arm and the vertical component of the bias force vector is the moment or torque applied to the spine 10, and the horizontal component of the bias force vector is the shear applied to the spine 10. Thus, in order to minimize curvature of the spine 10, all of the moments are balanced about the median plane 70 In order to minimize lateral bias on the spine 10, all of the horizontal components of the bias force vectors are balanced about the median plane 70. The easiest way to accomplish this result, of course, is to mount the dynamic bias devices 100 symmetrically about the median plane 70. However, those skilled in the art will recognize that asymmetric mounting arrangements that substantially meet these criteria are also possible.

Further, because most protrusions 56 are posterior, the dynamic bias device(s) 100 is/are preferably mounted posterior to the axis of curvature 60. This is advantageous because loss of disc height is most common in the posterior disc 50, the largest amount of mechanical advantage about the anterior disc is obtained posterior to the axis of curvature 60, and the posterior portions of the vertebrae are easiest to access less invasively. However, the dynamic bias device(s) 100 may be mounted at any position relative to the axis of curvature 60 depending on the location of the protrusion 56, as long as the dynamic bias device(s) 100 is/are near the median plane 70, substantially equidistant from the median plane 70, or otherwise symmetric about the median plane 70 as discussed above.

Given these criteria, there are many suitable mounting locations or attachment points for the dynamic bias device 100. Some of the possible attachment points are labeled A–N in FIGS. 1A and 1B. Attachment points A–G refer to the lumbar vertebrae 20 (L1–L5), and attachment points H–N refer to the sacral vertebrae 30 particularly S1). The attachment points A–G of the lumbar region 12 are equally applicable to the thoracic and cervical regions of the spine 10, which are not illustrated for purposes of simplicity only.

In the lumbar region 12, attachment points A and B refer to the left lateral and right lateral surfaces of the spinous process 24; attachment point C refers to the posterior surface of the spinous process 24; attachment points D and E refer to the posterior surfaces of the left and right laminae 23; and attachment points F and G refer to the distal ends of the left and right transverse processes 25.

In the sacrum 14, attachment points H and I refer to the left lateral and right lateral surfaces of the superior median sacral crest 31; attachment points K and L refer to the posterior surfaces of the sacral laminae 33 between the median sacral crest 31 and the intermediate sacral crests 32; and attachment points M and N refer to posterior surface between the intermediate sacral crests 32 and the lateral sacral crests 34.

A wide variety of sets of attachment points are possible, a non-exhaustive list of which is set forth herein. For single dynamic bias device 100 mounting, the nomenclature is $(X_1Y_1)$ where $X_1$ is the attachment point on vertebra X, and $Y_1$, is the attachment point on vertebra Y. For double dynamic bias device 100 mounting, the nomenclature is $(X_1Y_1, X_2Y_2)$ where $X_1$ is the attachment point of the first dynamic bias device 100 on vertebra X, $Y_1$ is the attachment point of the first dynamic bias device 100 on vertebra Y, $X_2$ is the attachment point of the second dynamic bias device 100 on vertebra X, and $Y_2$ is the attachment point of the second dynamic bias device 100 on vertebra Y. Vertebrae X and Y refer to any two different vertebrae, which are usually, but not necessarily, adjacent. In addition, vertebrae X and Y may be superior and inferior, respectively, or vice-versa.

To illustrate the attachment point nomenclature, reference may be made to FIGS. 4B and 5B. In FIG. 4B, a first dynamic bias device 100 is attached to the left lateral surface of the two spinous processes, and a second dynamic bias device 100 is attached to the right lateral surface of the two spinous processes. Thus, the set of attachment points for the arrangement of FIG. 4B is (AA, BB). In FIG. 5B, only one dynamic bias device 100 is attached to the posterior surface of the two spinous processes. Thus, the set of attachment points for the arrangement of FIG. 5B is (CC).

By way of example, not limitation, the following sets of attachment points may be used to satisfy the above-referenced criteria with regard to balancing moments and forces about the median plane 70. For single dynamic bias device 100 mounting: (CC); and (CJ) are preferred. For double dynamic bias device 100 mounting: (AA, BB); (DD, EE); (FF, GG); (AH, BI); (DK, EL); (FK, GL); (DM, EN); and (FM, GN) are preferred. Also for double dynamic bias device 100 mounting: (AD, BE); (AF, BG); (AK, BL); (AM, BN); (DH, EI); (DF, EG); (FH, GI); (CA, CB); (CH, CI); (CD, CE); (CF, CG); (CK, CL); (CM, CN); (JA, JB); (TH, JI); (JD, JE); and (JF, JG) are possible. For more than double mounting, any combination of these sets may be used. Generally, the more posterior the attachment points, the less invasive the procedure will be. Attachment points A, B, C, H and I are preferred for this reason. In addition, to avoid interfering with the motion of the vertebrae, the dynamic bias device 140 is preferably disposed laterally or posteriorly of the spinous processes 24, as opposed to under and between the spinous processes 24.

The dynamic bias device 100 may be attached to these points by conventional surgical techniques, except as described herein. The posterior musculature and connective tissues may be dissected to expose the desired attachment points. If desired, any disc protrusions 56 may be removed, in whole or in part, using a conventional discectomy procedure. Also if desired, any other abnormal spinal growths or protrusions may be removed. However, for many disc protrusions 56, it is anticipated that conventional traction or separation techniques may be employed to temporarily retract the protrusion 56 into the normal disc space until the dynamic bias devices are implanted.

In order to establish separation of the vertebrae, the spine may be placed in traction or conventional intervertebral separation tools may be used. Alternatively, the dynamic bias device 100 may be preloaded such that when the device is released after attachment, the bias force establishes the desired amount of separation.

Pilot holes are drilled as needed, such as for the use of bushings 330, 340 and/or 350 (described with reference to FIGS. 7A–7B, 8A–8B and 9A–9B hereinafter). If attachment points A, B, H and I are to be used, such as with the use of bushing 320 (described with reference to FIGS. 6A–6D hereinafter), a hole 90 and counter-bore 92 may be drilled into the spinous process 24. The device(s) 100 are then attached to the desired attachment points in accordance with the hardware being used, and the site is subsequently surgically closed.

With reference to FIGS. 6A–6D, 7A–7B, 8A–8B and 9A–9B, various embodiments of bushings 320, 330, 340, and 350, respectively, are illustrated. As mentioned previously, the attachment members 102 may comprise a wide variety of mechanical connection designs, and may incorporate into their design, or be used in combination with, other machine elements such as bushings 320, 330, 340, and 350. Bushings 320, 330, 340, and 350 are adapted to mount one or two dynamic bias devices 100. As illustrated, bushings 320, 330, 340, and 350 are adapted to receive attachment members 102 in the form of loops or the like, but may be modified to receive other structures. A primary function of bushings 320, 330, 340, and 350 is to isolate movement of the attachment members 102 from the vertebrae to which they are attached. Thus, the bushing to bone (vertebrae) interface is static, while the bushing to attachment member interface is dynamic. This reduces if not eliminates the abrasive degradation of the vertebrae due to the attachment of the dynamic bias device 100. The orientation of the vertebral surface at the attachment points will determine the best bushing scheme.

With reference to FIGS. 6A–6B, end and exploded views, respectively, of a bushing 320 are illustrated. Bushing 320 is particularly suitable for attachment to the spinous process 24 as shown in FIG. 6C, or attachment points A, B, H and I as illustrated in FIG. 1A. Bushing 320 may be attached to the spinous process 24 utilizing a conventional fastener 300, which includes bolt 302, nut 304 and washers 306 and 308. Preferably, the fastener 300 is a lock fastener such that it will not have a tendency to unscrew with relative motion of the attachment members 102. However, the nut 304 is not tightened so much as to inhibit rotational movement of the attachment members 102. Fastener 300 may alternatively comprise a key and pin (e.g., cotter pin). When fully assembled, the attachment members 102 are disposed around the shaft of the bolt 302 on either side of the bushing 320 and between the washers 306 and 308.

Bushing 320 includes a male fitting 321 which fits into a female fitting 324. The male fitting 321 includes a shank portion 322 and a head portion 323. Similarly, the female fitting 324 includes a shank portion 325 and a head portion 326. The female fitting 324 has an inside diameter sized to accommodate the shank 322 of the male fitting 321, and the male fitting 321 has an inside diameter sized to accommodate the bolt 302 of the fastener 300. The outside surface of the shank 322 of the male fitting 321 and the inside surface of the shank 325 of the female fitting 324 may include mating threads.

The size of the head 323/326 to bone interface is preferably maximized to minimize stress concentration and to distribute torsional loads over a large surface area. The size of the female shank 25 and the corresponding size of the hole 90 drilled through the spinous process 24 are chosen to minimize stress concentration and minimize the loss of bone integrity. A counter-bore 92 may be used to flatten and thereby maximize the contact surface area of the head 323/326 to bone interface, as illustrated in FIG. 6D.

The materials of the fastener 300 and bushing 320 may comprise any suitable implantable material capable of withstanding high fatigue. For example, all components could be comprised of 300 or 400 series stainless steel, titanium alloy 6-4, or MP35N alloy. Preferably, all components would be made of the same or similar material to reduce galvanic corrosion. The surfaces of the fastener 300 and bushing 320 that engage the attachment members 102 of the dynamic bias device 100 are preferably smooth to reduce friction and wear. The surfaces of the bushing 320 that engage the vertebrae may have a roughened surface (e.g., knurled) to reduce the likelihood of relative movement therebetween. In addition, the surfaces of the bushing 320 that engage the vertebrae may have a porous sintered surface to facilitate solid bone growth, thereby further securing the bushing 320. Coatings and surface treatments may be utilized to reduce or increase friction where desired, and biological response where tissue interface is likely.

With reference to FIGS. 7A–7B, end and exploded views, respectively, of a bushing 330 are illustrated. Except as described herein, bushing 330 is substantially the same in design, function and use as bushing 320. Bushing 330 is adapted to mount one or (preferably) two dynamic bias devices 100. Bushing 330 is particularly suitable for attachment points C and J as illustrated in FIG. 1B. Bushing 330 may be attached to the vertebrae 20/30 utilizing a conventional bone screw 310, which may be modified in diameter, length and thread type for the particular attachment site and condition.

Bushing 330 includes two male fittings 331 which fit into a female fitting 334. The male fittings 331 each include a shank portion 332 and a head portion 333. Similarly, the female fitting 334 includes two shank portions 335 and two head portions 336. The female fitting 334 has an inside diameter sized to accommodate the shanks 332 of the male fittings 331, and the male fittings 331 have an inside diameter sized to accommodate the bolt 302 of the fastener 300. The outside surfaces of the shanks 332 of the male fittings 331 and the inside surfaces of the shanks 335 of the female fitting 334 may include mating threads. When fully assembled, the attachment members 102 are disposed around the shanks 335 on either side of heads 336 of the female fitting 334 and between the heads 333 of the male fittings 331.

Figures 8A, 8B:
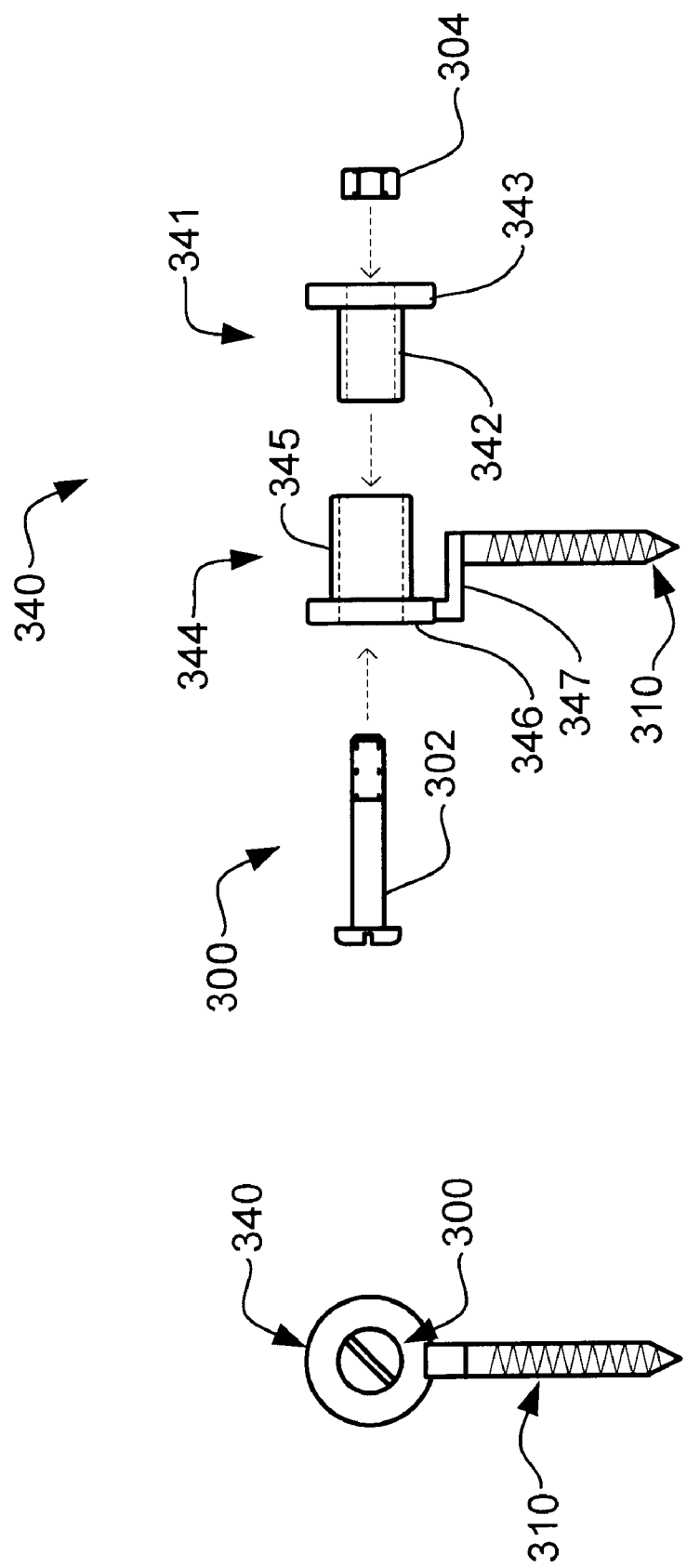
FIGS. 8A–8B illustrate end and exploded views, respectively, of a bushing in accordance with a third embodiment of the present invention.

With reference to FIGS. 8A–8B, end and exploded views, respectively, of a bushing 340 are illustrated. Except as described herein, bushing 340 is substantially the same in design, function and use as bushing 330. Bushing 340 is adapted to mount one dynamic bias device 100. Bushing 340 is particularly suitable for attachment points C, D, E, F, G, J, K, L, M and N, but may also be used for attachment points A, B, H and I as illustrated in FIGS. 1A and 1B. Bushing 340 may be attached to the vertebrae 20/30 utilizing a conventional bone screw 310, which may be modified in diameter, length and thread type for the particular attachment site and condition.

Bushing 340 includes a male fitting 341 which fits into a female fitting 344. The male fitting 341 includes a shank portion 342 and a head portion 343. Similarly, the female fitting 344 includes a shank portion 345 and a head portion 346. The female fitting 344 also includes a flange 347 connecting the bone screw 310 to the bushing 340. The female fitting 344 has an inside diameter sized to accommodate the shank 342 of the male fitting 341, and the male fitting 341 has an inside diameter sized to accommodate the bolt 302 of the fastener 300. The outside surface of the shank 342 of the male fitting 341 and the inside surface of the shank 345 of the female fitting 344 may include mating threads. When fully assembled, the attachment member 102 is disposed around the shank 345 on the female fitting 344 and between the heads 343/346 of the fittings 341/344. When mounted, the axis of the shank 345 of bushing 340 is oriented parallel to the mounting surface.

Figure 9B:
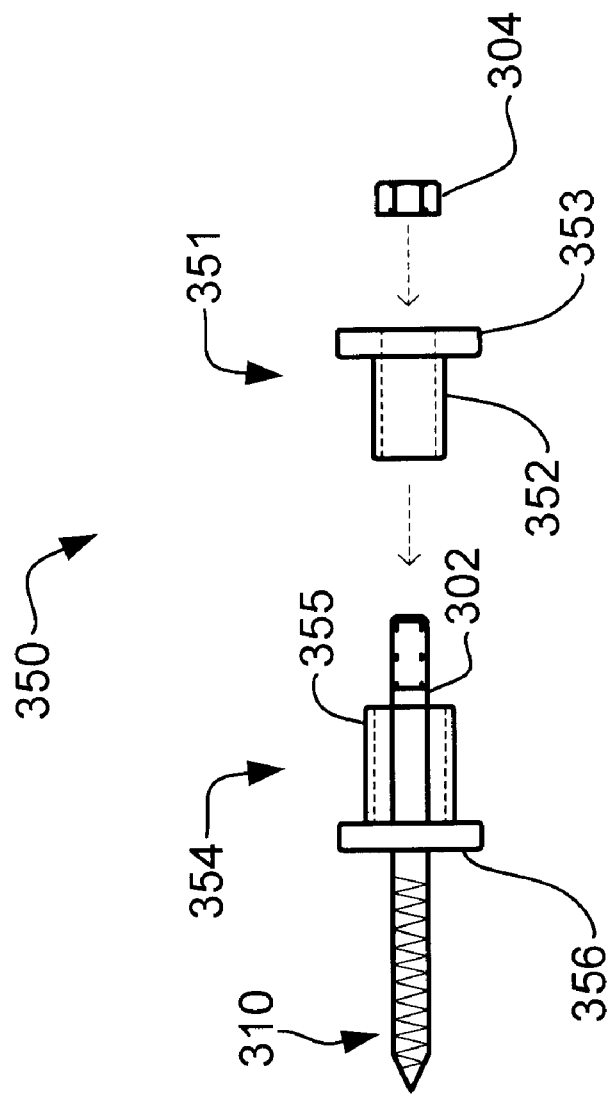
FIGS. 9A–9B illustrate end and exploded views, respectively, of a bushing in accordance with a fourth embodiment of the present invention.
Figure 9A:
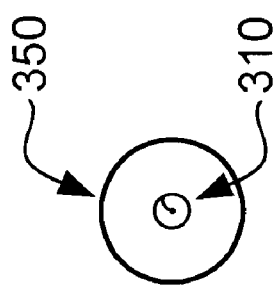

With reference to FIGS. 9A–9B, end and exploded views, respectively, of a bushing 350 are illustrated. Except as described herein, bushing 350 is substantially the same in design, function and use as bushing 340. Bushing 350 is adapted to mount one dynamic bias device 100. Bushing 350 is particularly suitable for attachment points C, D, E, F, G, J, K, L, M and N, but may also be used for attachment points A, B, H and I as illustrated in FIGS. 1A and 1B. Bushing 350 may be attached to the vertebrae 20/30 utilizing a conventional bone screw 310, which may be modified in diameter, length and thread type for the particular attachment site and condition. In this particular embodiment, the fastener 300 is formed integrally with the bone screw 310.

Bushing 350 includes a male fitting 351 which fits into a female fitting 354. The male fitting 351 includes a shank portion 352 and a head portion 353. Similarly, the female fitting 354 includes a shank portion 355 and a head portion 356. The female fitting 354 has an inside diameter sized to accommodate the shank 352 of the male fitting 351, and the male fitting 351 has an inside diameter sized to accommodate the bolt 302, which is integral with the bone screw 310. The outside surface of the shank 352 of the male fitting 351 and the inside surface of the shank 355 of the female fitting 354 may include mating threads. When fully assembled, the attachment member 102 is disposed around the shank 355 on the female fitting 354 and between the heads 353/356 of the fittings 351/354. When mounted, the axis of the shank 355 of bushing 350 is oriented perpendicular to the mounting surface.

Figure 10C:
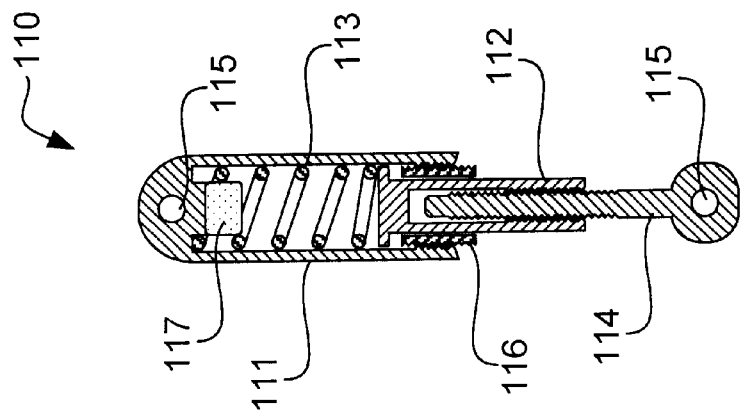
FIG. 10C illustrates a cross-sectional view of the dynamic bias device shown in FIG. 10A.
Figure 10B:
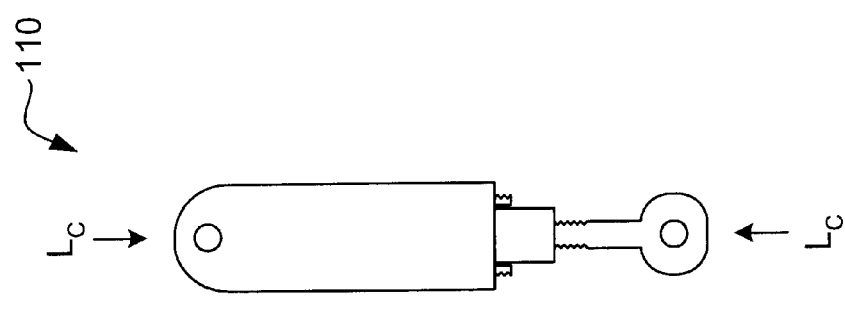
FIG. 10B illustrates a side view of the dynamic bias device shown in FIG. 10A subjected to a compression load.
Figure 10A:
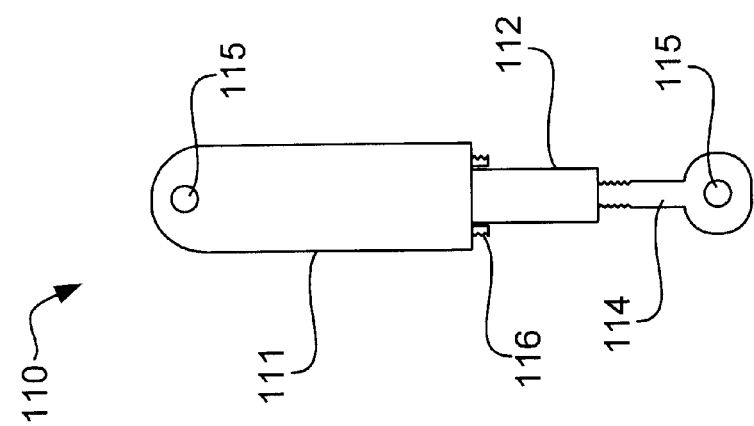
FIG. 10A illustrates a side view of a dynamic bias device in accordance with a first embodiment of the present invention.

With reference to FIGS. 10A–10C, side views of a dynamic bias device 110 are illustrated in a no-load condition, in a compression load condition, and in cross-section, respectively. Except as described herein, dynamic bias device 110 is substantially the same in design, function and use as the generic device 100 described previously. Dynamic bias device 1 10 includes a barrel 111 in which piston 112 is slidably disposed. A bias member in the form of a spring 113 is disposed in the barrel 111. Longitudinal displacement of the barrel 111 relative to the piston 112 causes compression (or extension) of the spring 113. The spring 113 provides a bias force which increases (or decreases) linearly with displacement as discussed previously. A flexible housing (not shown) may be placed about the dynamic bias device 110 to isolate the moving parts 111/112 from the surrounding tissue when implanted.

An adjustable arm 114 may be connected to the piston 112. The arm 114 and the barrel 111 include holes 115 or other suitable attachment members, which may be used in combination bushings 320, 330, 340 and 350, to attach the dynamic bias device 110 to the vertebrae. The adjustable arm 114 and the piston 112 may include mating threads such that rotation of the arm 114 causes the arm 114 to effectively lengthen or shorten the piston 112. This allows the distance between the holes 115 to be varied to accommodate different attachment locations and different anatomies. This also allows the dynamic bias device to be preloaded by extending the effective length of the piston 112 beyond the distance between attachment points.

A collar 116 is provided to limit the extended length of the dynamic bias device 110. The collar 116 may include threads that mate with threads inside the barrel 111 such that the collar 116 is adjustable, and thus the extended length is adjustable. The collar 116 may also include an elastomeric bumper pad to dampen impact between the piston 112 and the collar when the device 110 is fully extended. Similarly, a elastomeric bumper pad 117 may be provided in the barrel 111 to dampen impact between the piston 112 and the barrel 111 when the device 110 is fully collapsed.

Figure 11B:
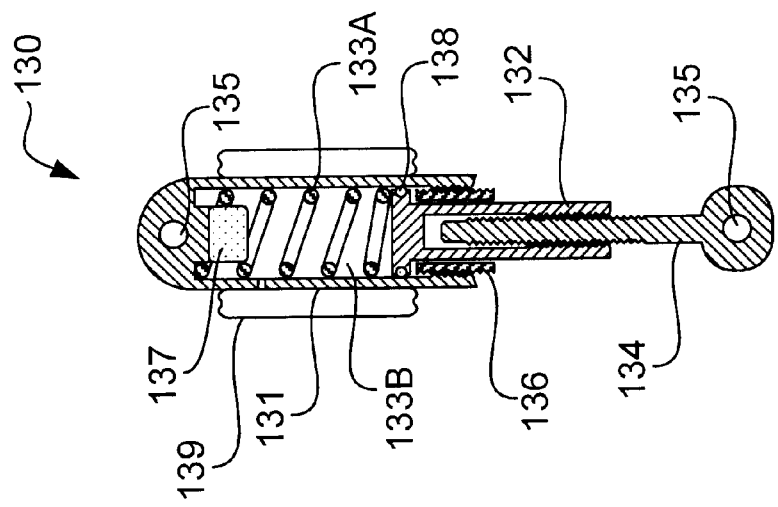
FIG. 11B illustrates a cross-sectional view of a dynamic bias device in accordance with a third embodiment of the present invention.
Figure 11A:
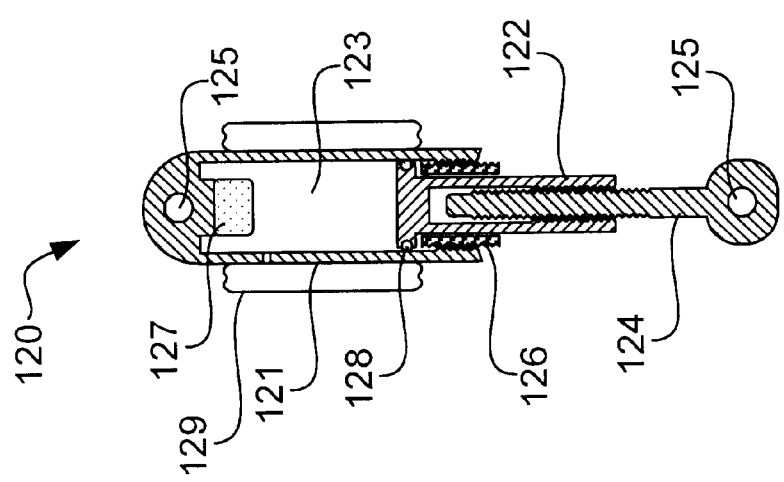
FIG. 11A illustrates a cross-sectional view of a dynamic bias device in accordance with a second embodiment of the present invention.

With reference to FIG. 11A, a cross-sectional view of a dynamic bias device 120 is illustrated. Except as described herein, dynamic bias device 120 is substantially the same in design, function and use as dynamic bias device 110 discussed with reference to FIGS. 10A–10C. Dynamic bias device 120 includes a barrel 121 in which piston 122 is slidably disposed. A bias member 123 in the form of a compressed or evacuated fluid (liquid or gas or a combination of both) is disposed in the barrel 121 and sealed relative to the piston 122 by piston ring 128. The barrel 121 and piston 122 may define a closed volume or an exhaust reservoir 129 may be used as shown. The bias fluid 123 is in fluid communication with the exhaust reservoir 129 by way of an exhaust port through the wall of the barrel 121. The exhaust reservoir 129 may comprise an expandable annular bag as shown, or other suitable structure. If a closed volume is used, longitudinal displacement of the barrel 121 relative to the piston 122 simply causes a change in pressure of the fluid 123. If an exhaust reservoir 129 is used as shown, longitudinal displacement of the barrel 121 relative to the piston 122 causes a change in pressure of the fluid 123 and flow of fluid 123 into the exhaust reservoir 129 via the exhaust port. The pressure of the fluid 123 and the size of the exhaust hole dictates the bias force which increases (or decreases) with the time derivative of displacement as discussed previously.

A flexible housing (not shown) may be placed about the dynamic bias device 130 to isolate the moving parts 121/122 from the surrounding tissue when implanted. The housing may be used to define the exhaust reservoir 129. An adjustable arm 124 may be connected to the piston 122. The arm 124 and the barrel 121 include holes 125 or other suitable attachment members to attach the dynamic bias device 120 to the vertebrae. The adjustable arm 124 and the piston 122 may include mating threads to effectively lengthen or shorten the piston 122. An adjustable collar 126 may be provided including mating threads such that the collar 126 is adjustable, and thus the extended length of the dynamic bias device 120 is adjustable. The collar 126 may include an elastomeric bumper pad (not shown) and an elastomeric bumper pad 127 may be provided in the barrel 121 to dampen impact between the piston 122 and the barrel 121.

With reference to FIG. 11B, a cross-sectional view of a dynamic bias device 130 is illustrated. Except as described herein, dynamic bias device 130 is substantially the same in design, function and use as the combination of dynamic bias device 110 discussed with reference to FIG. 10A–10C and dynamic bias device 120 described with reference to FIG. 11A.

Dynamic bias device 130 includes a barrel 131 in which piston 132 is slidably disposed. A bias member is the form of a spring 113A is disposed in the barrel 131. Longitudinal displacement of the barrel 131 relative to the piston 132 causes compression (or extension) of the spring 133. The spring 133 provides a bias force which increases (or decreases) linearly with displacement as discussed previously. In addition, a bias member 133B in the form of a compressed or evacuated fluid (liquid or gas) is disposed in the barrel 131 and sealed relative to the piston 132 by piston ring 138.

The barrel 131 and piston 132 may define a closed volume or an exhaust reservoir 129 may be used as shown. The bias fluid 133 is in fluid communication with the exhaust reservoir 139 by way of an exhaust port through the wall of the barrel 131. The exhaust reservoir 139 may comprise an expandable annular bag as shown, or other suitable structure. If a closed volume is used, longitudinal displacement of the barrel 131 relative to the piston 132 simply causes a change in pressure of the fluid 133. If an exhaust reservoir 139 is used as shown, longitudinal displacement of the barrel 131 relative to the piston 132 causes a change in pressure of the fluid 133 and flow of fluid 133 into the exhaust reservoir 139 via the exhaust port. The pressure of the fluid 133 and the size of the exhaust hole dictates the bias force which increases (or decreases) with the time derivative of displacement as discussed previously. Thus, the bias members 133A/133B effectively act as a combined spring and damper.

A flexible housing (not shown) may be placed about the dynamic bias device 130 to isolate the moving parts 131/132 from the surrounding tissue when implanted. The housing may be used to define the exhaust reservoir 139. An adjustable arm 134 may be connected to the piston 132. The arm 134 and the barrel 131 include holes 135 or other suitable attachment members to attach the dynamic bias device 130 to the vertebrae. The adjustable arm 134 and the piston 132 may include mating threads to effectively lengthen or shorten the piston 132. An adjustable collar 136 may be provided including mating threads such that the collar 136 is adjustable, and thus the extended length of the dynamic bias device 130 is adjustable. The collar 136 may include an elastomeric bumper pad (not shown) and an elastomeric bumper pad 137 may be provided in the barrel 131 to dampen impact between the piston 132 and the barrel 131.

Figure 12C:
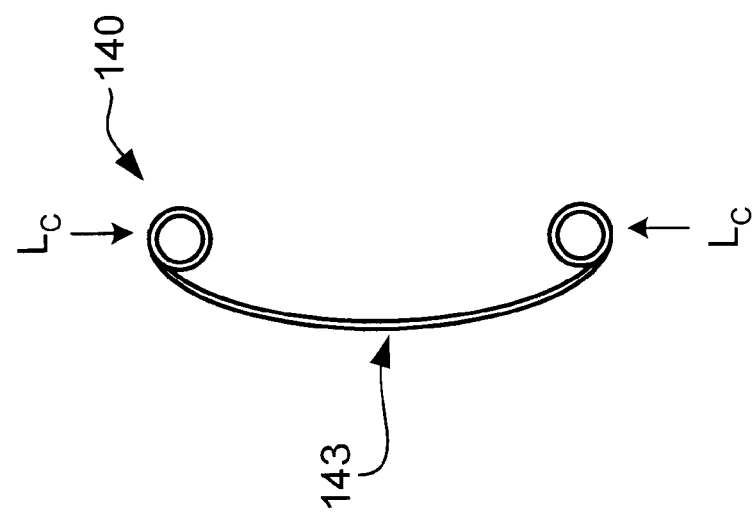
FIG. 12C illustrates the dynamic bias device shown in FIGS. 12A–12B subjected to a compression load.
Figure 12B:
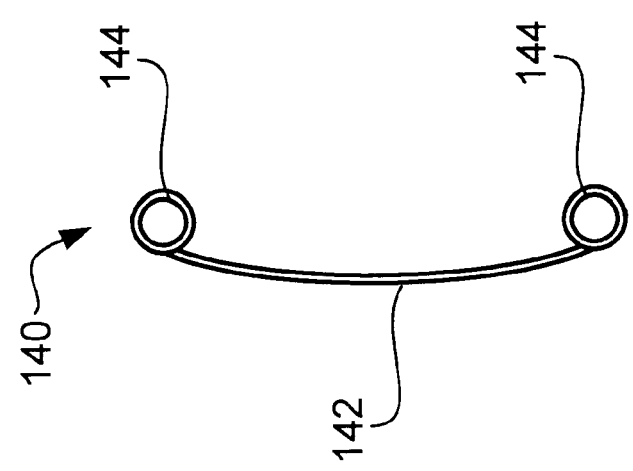
FIGS. 12A–12B illustrate rear and side views, respectively, of a dynamic bias device in accordance with a fourth embodiment of the present invention.
Figure 12A:
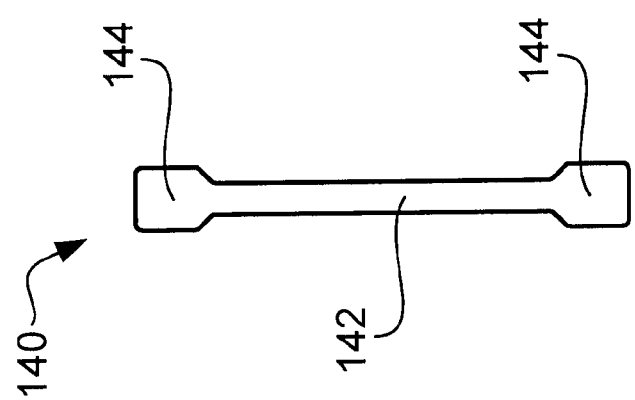

With reference to FIGS. 12A–12B, rear and side views of dynamic bias device 140 are illustrated in no-load condition. FIG. 12C illustrates the dynamic bias device 140 subjected to a compression load. Except as described herein, dynamic bias device 140 is substantially the same in design, function and use as the generic device 100 described previously. Although movement of the dynamic bias device 140 in compression and extension is substantially linear and parallel to the axis of curvature 60, as with dynamic bias device 100, some lateral or posterior-anterior motion is present, but preferably minimized. Dynamic bias device 140 includes bias member 142 and loops 144 or other suitable attachment members, which may be used in combination bushings 320, 330, 340 and 350, to attach the dynamic bias device 140 to the vertebrae. The bias member 142 is may be a semi-circular or semi-elliptical leaf spring, which may be a single plate as shown or a series of laminated plates. Relative longitudinal displacement of the attachment members 144 causes compression (or extension) of the leaf spring 142. The leaf spring 142 provides a bias force which increases (or decreases) with displacement as discussed previously.

The radius or axis of curvature of the leaf spring 142 is preferably maximized such that displacement of the attachment members 144 is substantially linear, but should not be so high as to result in buckling or inversion in compression. By way of example, not limitation, the radius or axis of curvature may range from half the distance between the attachment points to approximately 10 cm. Of course, half the distance between attachment points will vary depending on the location of each attachment point, but will likely be in the range of 1.0 to 3.0 cm for attachment points between adjacent processes.

The displacement of the apex 143 is preferably of the leaf spring 142 minimized to minimize disturbance of and interference from surrounding tissue (bone, muscle, connective tissue, nerves, etc.). The apex 143 may face anteriorly, but preferably faces posteriorly or laterally to reduce interference with tissue close to the spinal column. The dynamic bias device 140, and particularly the leaf spring 142, is preferably disposed laterally or posteriorly of the spinous processes 24 to avoid interference with movement of the vertebrae.

With reference to FIGS. 13A–13C, various alternative dynamic bias devices 150, 160 and 170 are illustrated in side and posterior views. Except as described herein, dynamic bias devices 150, 160 and 170 are substantially the same in design, function and use as the dynamic bias device 140 discussed with reference to FIGS. 12A–12C.

Dynamic bias device 150 as seen in FIG. 13A includes bias member 152 in the form of an articulated leaf spring, and attachment members 154. Articulated leaf spring 152 reduces the horizontal range of movement by utilizing a plurality of articulations 153 having a smaller radius or axis of curvature. The reduced horizontal range of movement of the bias member 152 reduces the amount of disturbance and interference from surrounding tissue (bone, muscle, connective tissue, nerves, etc.).

Dynamic bias device 160 as seen in FIG. 13B includes a plurality of bias members 162 in the form of leaf springs (shown) or articulated leaf springs (not shown), and attachment members 164. Utilizing a plurality of leaf springs 162 increases stability of the dynamic bias device 160 and allows for greater net bias forces to be delivered to the attachment members 164 and the vertebrae attached thereto.

Dynamic bias device 170 as seen in FIG. 13C includes a plurality of bias members 172 in the form of leaf springs (shown) or articulated leaf springs (not shown). The dynamic bias device 170 also includes attachment members 174 in the form of inverted semi-circular loops. The inverted semi-circular loops 174 permit the device 170 to be attached to the inferior and superior sides spinous processes of adjacent vertebrae, such that the attachment members 174 are disposed between adjacent spinous processes but the bias members 172 are disposed laterally of the spinous processes to avoid interference with movement of the vertebrae.

Dynamic bias devices 110, 120, 130, 140, 150, 160 and 170 may be used (i.e., implanted) substantially as described with reference to generic dynamic bias device 100. As mentioned previously, one or more reinforcement members 200 may be used in combination with one or more dynamic bias devices 100. The reinforcement members 200 may be used to reinforce the disc, restore disc height and/or bear some or all of the load normally carried by the annulus. The reinforcement members 200 are relatively rigid and thus serve to reinforce the disc 50, and particularly the annulus 52, where inserted. In addition, the reinforcement members 200 may have a relatively large profile when implanted and thus increase disc height.

Figure 15D:
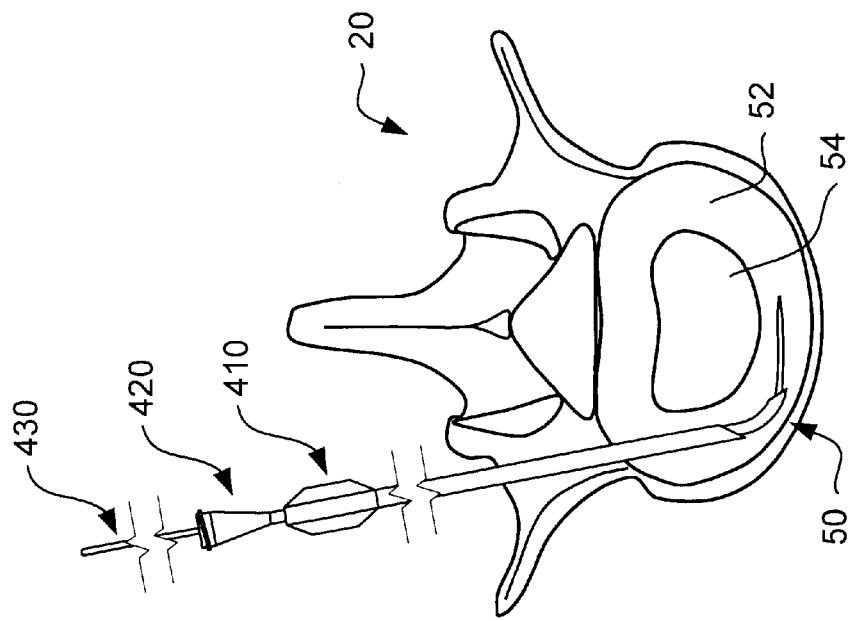
Figure 15C:
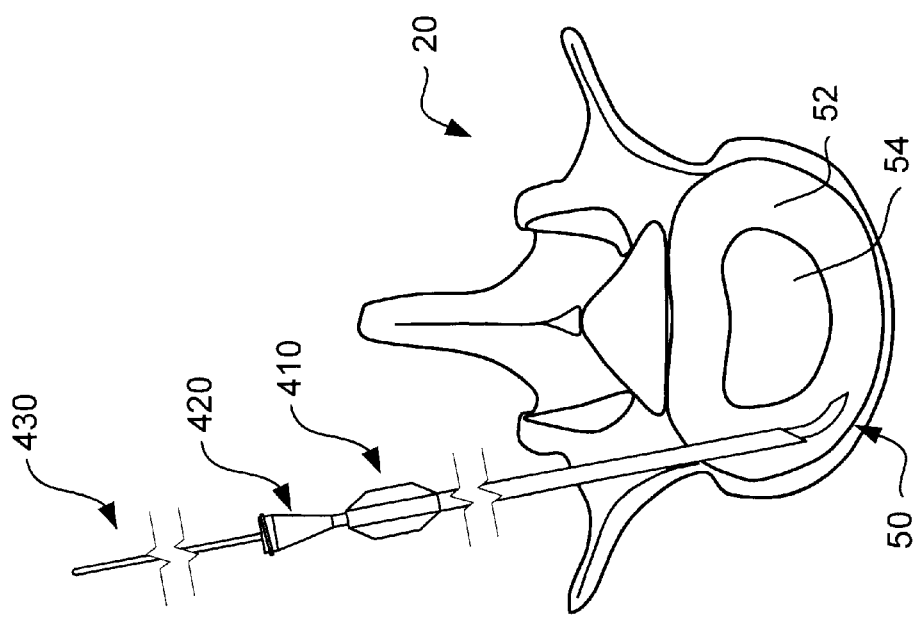

The reinforcing members 200 may be used singularly or in groups, depending on the increase in disc 50 height desired and/or the amount of reinforcement of the annulus 52 desired. For example, the reinforcing members 200 may be stacked as illustrated in FIG. 2B or inserted side-by-side as illustrated in FIG. 15R. In addition, the reinforcing members 200 may be located in virtually any portion of the annulus 52. Preferably, the reinforcing members 200 are substantially symmetrically disposed about the median plane 70 to avoid causing curvature of the spine 10. Although the reinforcing members 200 may be inserted, in part or in whole, into the nucleus 54, it is preferable to insert them into the annulus 52 for purposes of stability and load carrying. Specifically, to provide stability, it is desirable to symmetrically locate the reinforcing members 200 as far as reasonably possible from the median plane 70, or to span as great a distance as possible across the median plane 70. In addition, because the annulus 52 of the disc 50 is believed to carry the majority of the load, particularly in the lumbar region 12, the reinforcing members 200 are preferably placed in the annulus 52 to assume the load normally carried thereby, and reinforce the load bearing capacity of the annulus 52, without hindering the normal mobility function of the disc 50.

The reinforcing members 200 may comprise expandable members such as self-expanding members 210 or inflatable members 220. Alternatively, the reinforcing members 200 may comprise unexpandable members such as reinforcement bars 230. When implanting each type of reinforcement member 210/220/230, it is preferable to maintain the integrity of the annulus 52. Accordingly, space in the annulus 52 for the reinforcing members 200 is preferably established by dilation or the like, although some amount of tissue removal may be used.

The expandable reinforcement members 210/220 are useful because they may be delivered in a low profile, unexpanded condition making it easier to traverse the very tough and fibrous collagen tissue of the annulus 52. For similar reasons, the reinforcement bars 230 are useful because they may have a small diameter and a sharpened tip. Although it is possible to insert the expandable reinforcing members 210/220 into the annulus 52 in their final expanded state, it is desirable to deliver the expandable reinforcing members 210/220 into the annulus 52 in an unexpanded state and subsequently expand them in order to minimize invasiveness and resistance to insertion.

The self-expanding reinforcing member 210 may comprise a solid or semi-solid member that self-expands (e.g., by hydration) after insertion into the annulus. Examples of suitable materials for such solid or semi-solid members include solid fibrous collagen or other suitable hard hydrophilic biocompatible material. If the selected material is degradable, the material may induce the formation of fibrous scar tissue which is favorable. If non-degradable material is selected, the material must be rigid and bio-inert. The self-expanding reinforcing member 210 preferably has an initial diameter that is minimized, but may be in the range of 25% to 75% of the final expanded diameter, which may be in the range of 0.3 to 0.75 cm, or 10% to 75% of the nominal disc height. The length of the self-expanding member 210 may be in the range of 1.0 to 6.0 cm, and preferably in the range of 2.0 to 4.0 cm.

The inflatable reinforcing member 220 may comprise an expandable hollow membrane capable of inflation after insertion into the annulus. An example of a suitable inflatable structure is detachable balloon membrane filled with a curable material. The membrane may consist of a biocompatible and bio-inert polymer material, such as polyurethane, silicone, or polycarbonate-polyurethane (e.g., Corethane). The curable filler material may consist of a curable silicone or polyurethane. The filler material may be curable by chemical reaction (e.g., moisture), photo-activation (e.g., UV light) or the like. The cure time is preferably sufficiently long to enable activation just prior to insertion (i.e., outside the body) and permit sufficient time for navigation and positioning of the member 220 in the disc. However, activation may also take place inside the body after implantation. The inflatable reinforcing member 220 preferably has an initial deflated diameter that is minimized, but may be in the range of 25% to 75% of the final inflated diameter, which may be in the range of 0.3 to 0.75 cm, or 10% to 75% of the nominal disc height. The length of the inflatable member 220 may be in the range of 1.0 to 6.0 cm, and preferably in the range of 2.0 to 4.0 cm.

The reinforcement bars 230 may comprise a rigid, solid or hollow bar having a sharpened tip. The reinforcement bars 230 may comprises stainless steel mandrels, for example, having a diameter in the range of 0.005 to 0.100 inches, preferably in the range of 0.010 to 0.050 inches, and most preferably in the range of 0.020 to 0.040 inches, and a length in the range of 1.0 to 6.0 cm, and preferably in the range of 2.0 to 4.0 cm. The reinforcement bars 230 may be straight for linear insertion, or curved to gently wrap with the curvature of the annulus during insertion. In addition, the outer surface of the reinforcement bars 230 may have circular ridges or the like that the permit easy insertion into the annulus 52 but resist withdrawal and motion in the annulus following implantation. Other suitable materials for reinforcement bars 230 include titanium alloy 6-4, MP35N alloy, or super-elastic nickel-titanium alloy.

Figure 14A:
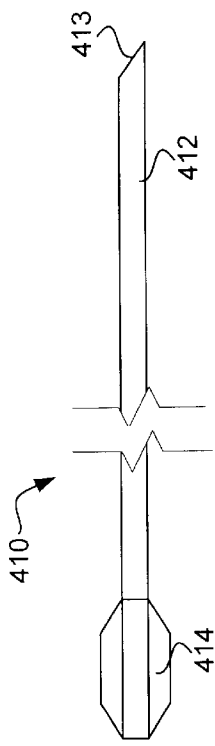
FIGS. 14A–14D illustrate tools of the present invention for implanting the reinforcement members.
Figure 14B:
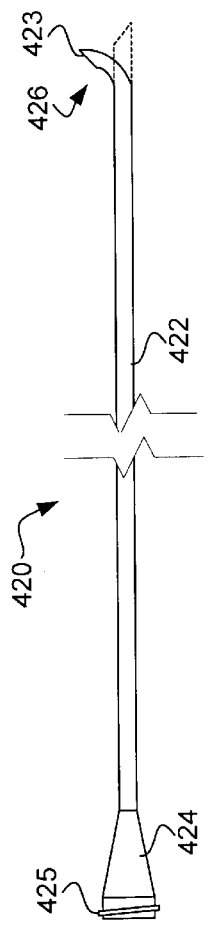
Figure 14C:
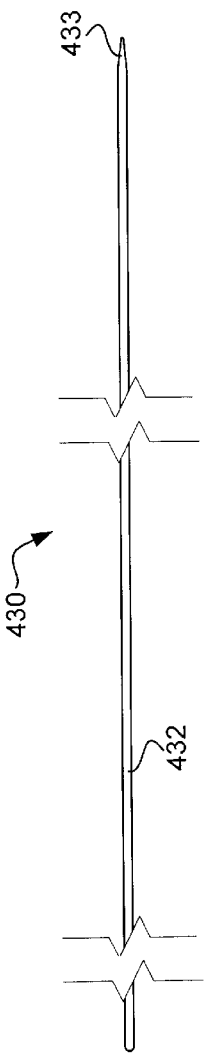
Figure 14D:
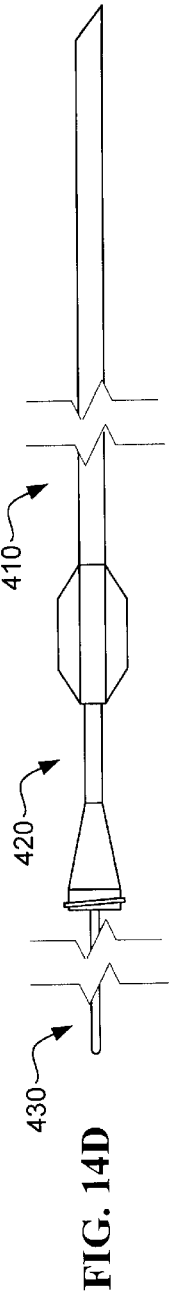

Referring now to FIGS. 14A–14D, various tools 410, 420 and 430 are shown individually and assembled. The tools 410, 420 and 430 may be used to implant the reinforcement devices 210/220/230 discussed above. The tools include a rigid, sharpened, hollow needle 410, a semi-rigid, sharpened, hollow curved needle 420, and a sharpened stylet 430. As seen in FIG. 14D, the sharpened stylet 430 fits into the semi-rigid needle 420 which fits into the rigid needle 410.

With specific reference to FIG. 14A, the rigid hollow needle 410 includes a hollow shaft 412 and a grip or handle 414. The shaft 412 includes a sharpened tip 413 to facilitate insertion into and pass through the surrounding tissue. The shaft 412 is preferably made of a rigid metal such as a stainless steel hypodermic tube. The grip 414 may comprise a polymer and may be formed by insert injection molding with the shaft 412 inserted into the mold.

With specific reference to FIG. 14B, the semi-rigid curved needle 420 includes a hollow shaft 422 a hub 424. The shaft 422, which includes a sharpened tip 423, is longer than the rigid needle 410 and has an outside diameter sufficiently small to fit into the rigid needle 410. The shaft 422 is preferably made of a semi-rigid polymer or composite. The shaft 422 includes a curved distal portion 426 that may be straightened (shown in phantom) upon insertion of the semi-rigid needle 420 into the lumen of the rigid needle 410. The hub 424 may include a fitting 425 to facilitate connection to a fluid source or a pressure source (e.g., a syringe).

With specific reference to FIG. 14C, the sharpened stylet 430 includes a flexible shaft 432 and a sharpened distal end 433. The shaft 432 is longer than the both the rigid needle 410 and the semi-rigid needle 420, and may have a length on the order of 10 to 60 cm. The shaft 432 also has an outside diameter sufficiently small to fit into the semi-rigid needle 420. The shaft 422 preferably has a flexible but pushable construction incorporating a rigid metal such as stainless steel, or super-elastic nickel-titanium alloy. The sharpened stylet 430 is preferably highly elastic, to resist permanent set upon insertion into the curved portion 426 of the semi-rigid needle 420.

With general reference to FIGS. 15A–15J, the steps for implanting a self-expanding reinforcement member 210 are illustrated. It should be understood that the procedure for implanting a single member 210 in the anterior annulus 52 is shown for purposes of illustration, not limitation. All of the variables with regard to quantity, location, orientation, etc. discussed previously may be implemented by varying the generic procedure described hereinafter.

Initially, the sharpened stylet 430, semi-rigid needle 420 and rigid needle 410 are assembled as shown in FIG. 14D. As shown in FIG. 15A, the distal portion of the assembly 410/420/430 is inserted into the disc 50 as in a conventional discogram procedure. The assembly 410/420/430 is advanced until the distal tip 413 of the rigid needle is proximate the anterior curvature of the annulus 52, near the anterior side of the nucleus 54, as seen in FIG. 15B. The semi-rigid needle 420 (alone or with stylet 430) is advanced relative to the rigid needle 410 until the curved portion 426 of the semi-rigid needle exits the distal tip 413 of the rigid needle 410 and the desired amount of curvature is established, as seen in FIG. 15C. The curved portion 426 may be advanced until the tip 423 is substantially parallel to the tangent of the anterior annulus 52 curvature. The sharpened stylet 430 is advanced relative to the semi-rigid needle 420 to the desired position within the anterior annulus 52, as shown in FIG. 15D. The semi-rigid needle 420 and the rigid needle 410 are completely withdrawn from the stylet 430, leaving the stylet in position as shown in FIG. 15E.

Figure 15F:
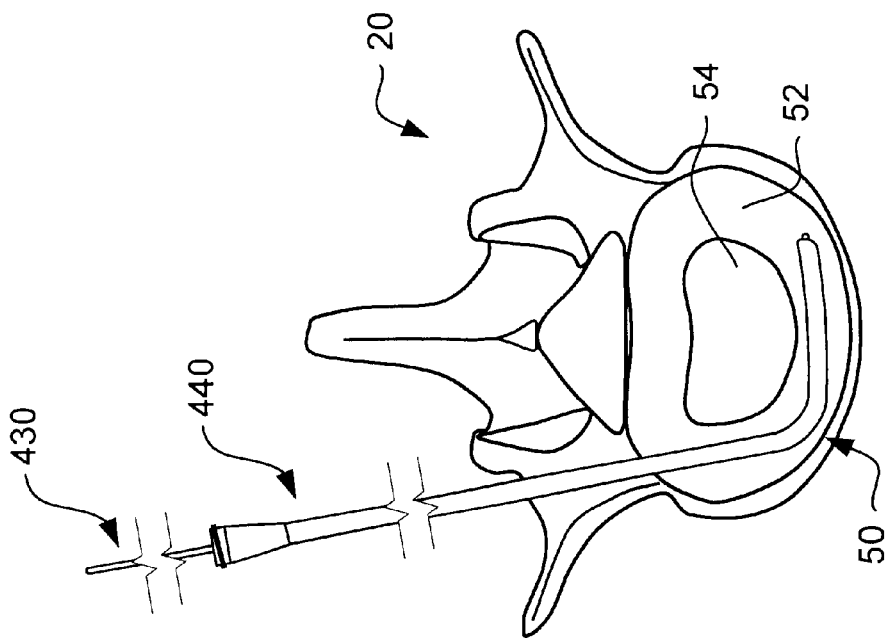
Figure 15E:
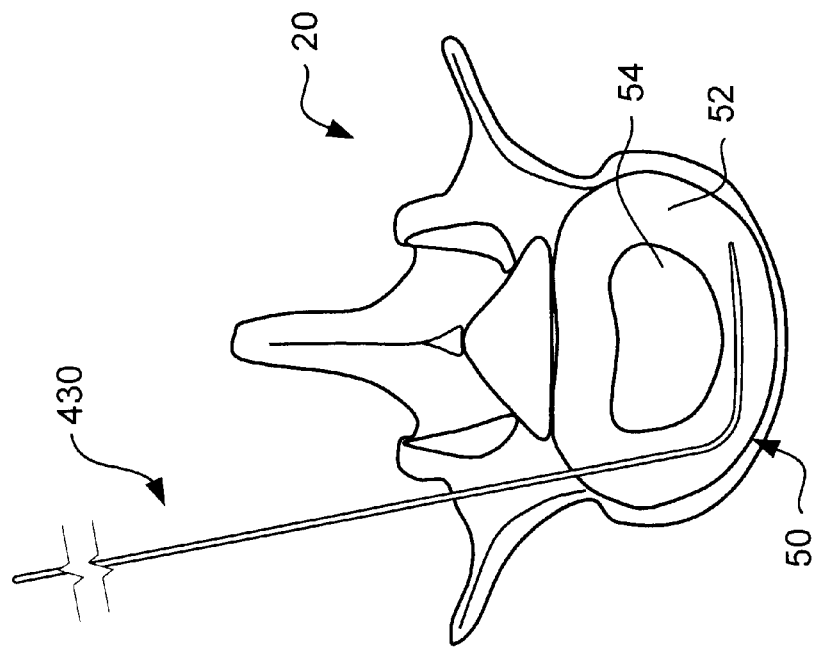
Figure 15H:
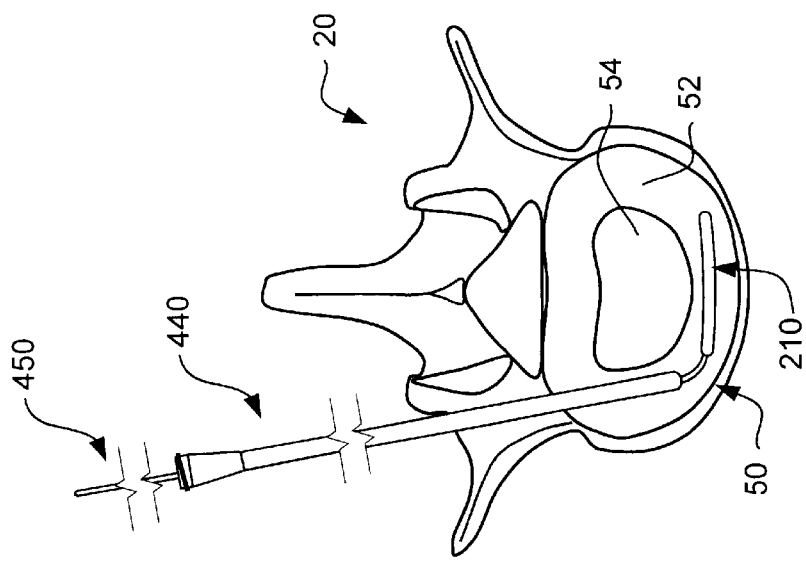
Figure 15G:
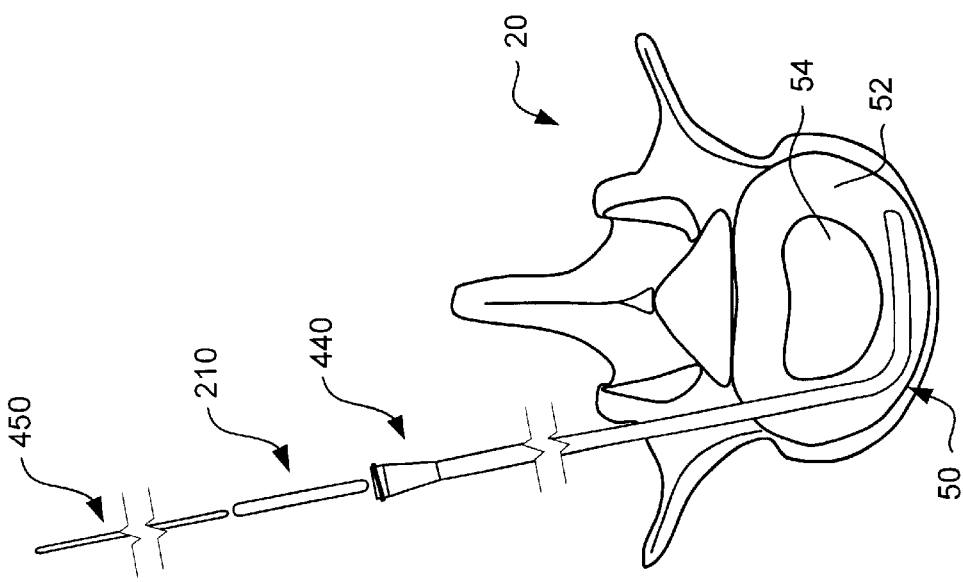
Figure 15J:
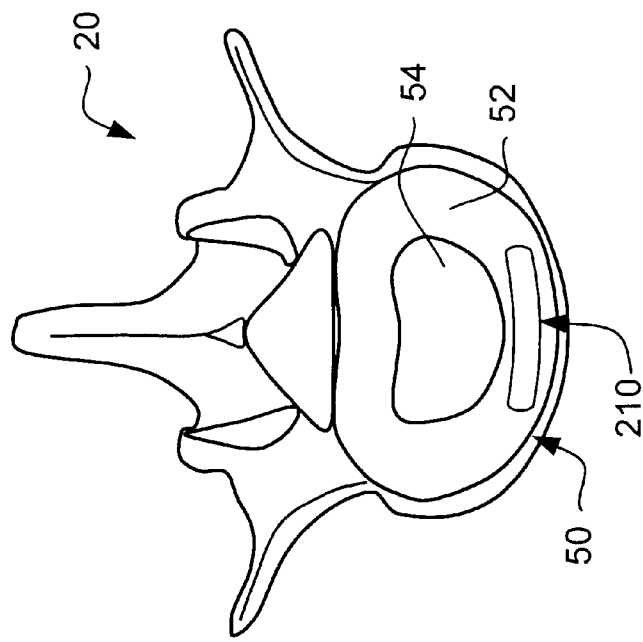
Figure 15I:
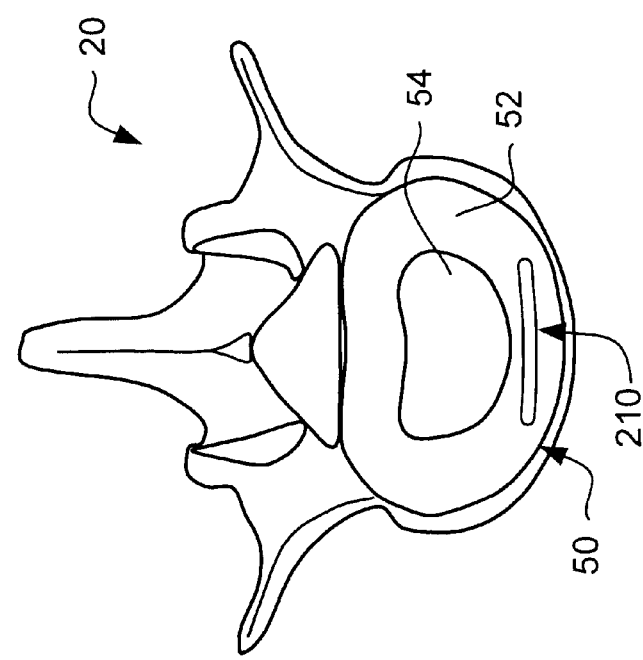

A flexible dilator 440 is advanced over the stylet 430 to dilate the annulus 52, as seen in FIG. 15F. The flexible dilator 440 is similar to semi-rigid needle 420 except that the dilator includes a blunt distal tip and is relatively more flexible, and has larger inner and outer diameters. Note that one or more dilators 440 may be advanced co-axially about the stylet 430 until the annulus is sufficiently dilated to accept the self-expandable member 210. The stylet 430 is then withdrawn from the flexible dilator 440 and the self-expandable member 210 is introduced into the lumen of the flexible dilator 440 using a push bar 450, as shown in FIG. 15G. Alternatively, the dilator 440 may be removed in favor of a flexible hollow catheter with a large inner diameter to facilitate delivery of member 210. The push bar 450 is similar to stylet 430 except that the distal tip of the push bar 450 is blunt. Alternatively, the push bar 450 may simply comprise the stylet 430 turned around, thus using the proximal blunt end of the stylet 430 as the push bar 450. The push bar 450 is advanced until the member 210 is in the desired position, as seen in FIG. 15H. To facilitate positioning the member 210, radiographic visualization may be used to visualize the distal end of the push bar 450, which is formed of radiopaque material and may include radiopaque markers. In addition, the member may be loaded with a radiopaque material to facilitate radiographic visualization thereof.

After the member 210 is in the desired position, the flexible dilator 440 is retracted from the push bar 450 while maintaining position of the member 210 with the push bar. The push bar 450 is then removed leaving the member 210 in place. If necessary, the procedure may be repeated for additional member implants 210. The member 210 is then allowed to expand over time, perhaps augmented by placing the spine 10 in traction. Alternatively, the spine 10 may be placed in traction prior to beginning the procedure as discussed with reference to the procedure for implanting dynamic bias device 100.

Figure 15L:
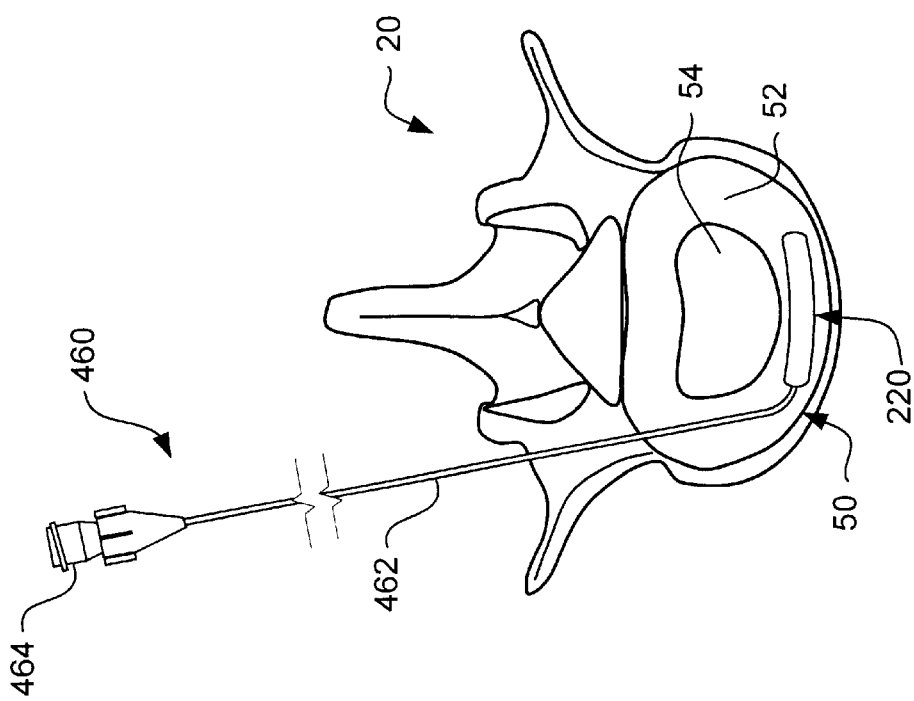
FIGS. 15K–15L illustrate steps for implanting an inflatable reinforcement member.
Figure 15K:
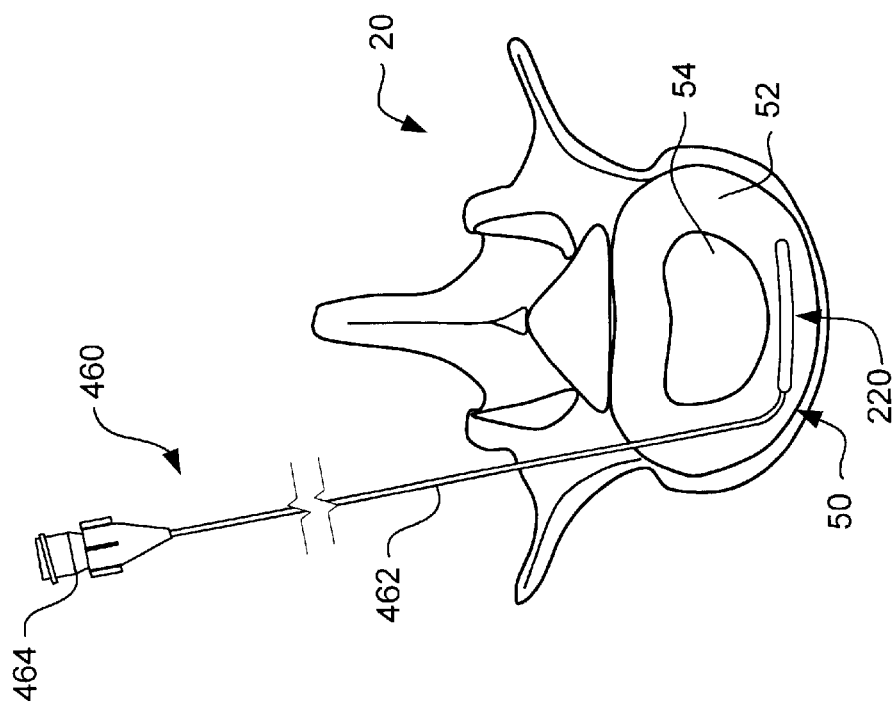

With reference to FIGS. 15K–15L, the steps for implanting an inflatable reinforcement member 220 are illustrated. In this procedure, the steps outlined with reference to FIGS. 15A–15F are followed. Specifically, the same steps are followed up to and including the step of advancing the flexible dilator 440 over the stylet 430 to dilate the annulus 52, and thereafter removing the stylet 430 from the flexible dilator 440. Using a catheter 460, the inflatable member 220 is introduced into the dilator 440 and advanced until the member 220 is in the desired position, as shown in FIG. 15K. The inflatable member 220 is connected to the distal end of the catheter 460, which includes a flexible but pushable shaft 462 and an inflation port 464. The flexible dilator 440 is retracted from the catheter 460 while maintaining position of the member 220.

With the member 220 in the desired position, which may be confirmed using radiographic visualization as described above, the proximal inflation port 464 is connected to a syringe (not shown) or other suitable inflation apparatus for injection of the curable filler material. The filler material is then activated and the desired volume is injected into the catheter 460 via the inflation port 464, as seen if FIG. 15L. The filler material is allowed to cure and the catheter 460 is gently torqued to break the catheter 460 from the solid member 220. This break-away step may be facilitated by an area of weakness at the juncture between the distal end of the catheter 460 and the proximal end of the member 220. The catheter 460 is then removed leaving the member 220 in place. If necessary, the procedure may be repeated for additional member implants 220.

Figure 15N:
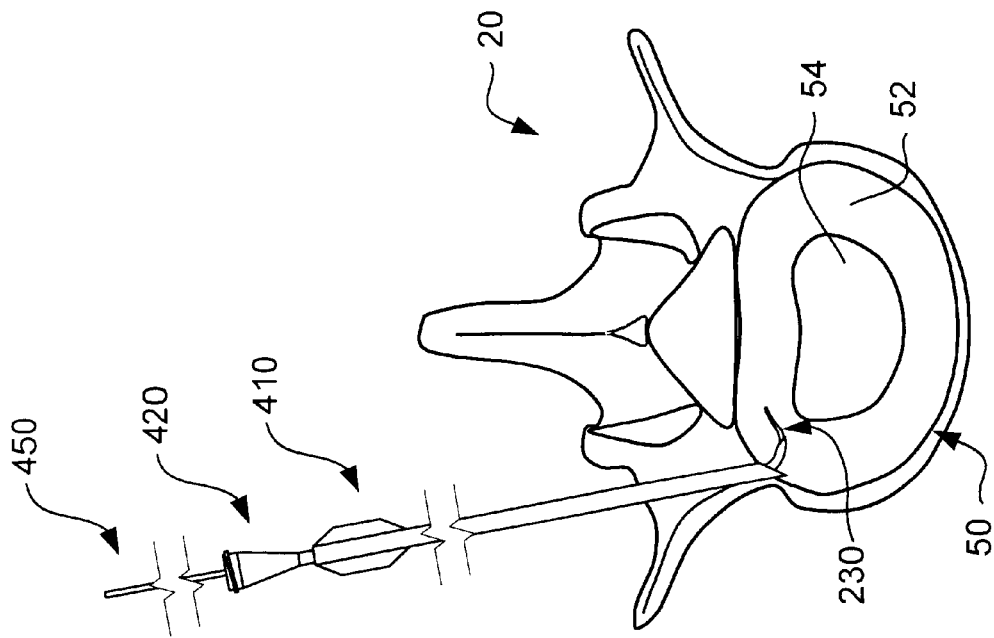
FIGS. 15M–15R illustrate steps for implanting reinforcement bars.
Figure 15M:
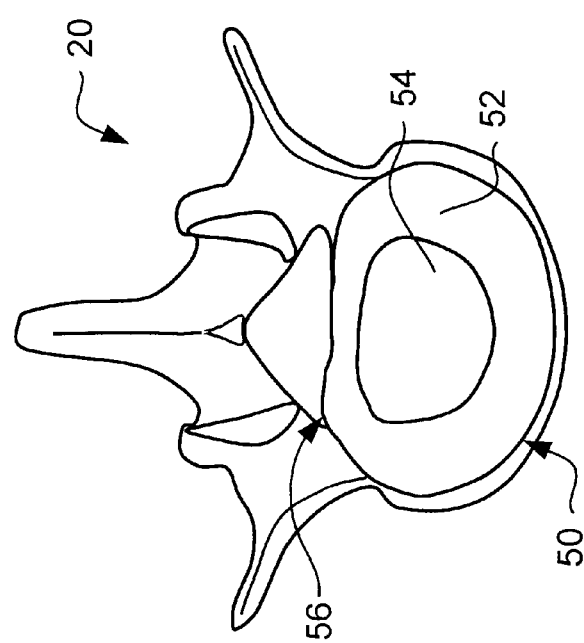
Figure 15P:
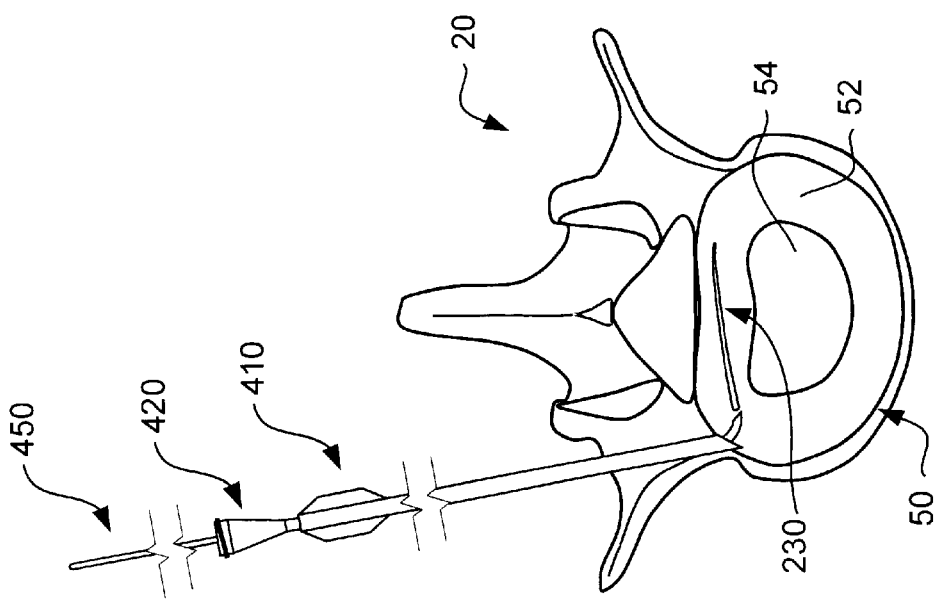
Figure 15O:
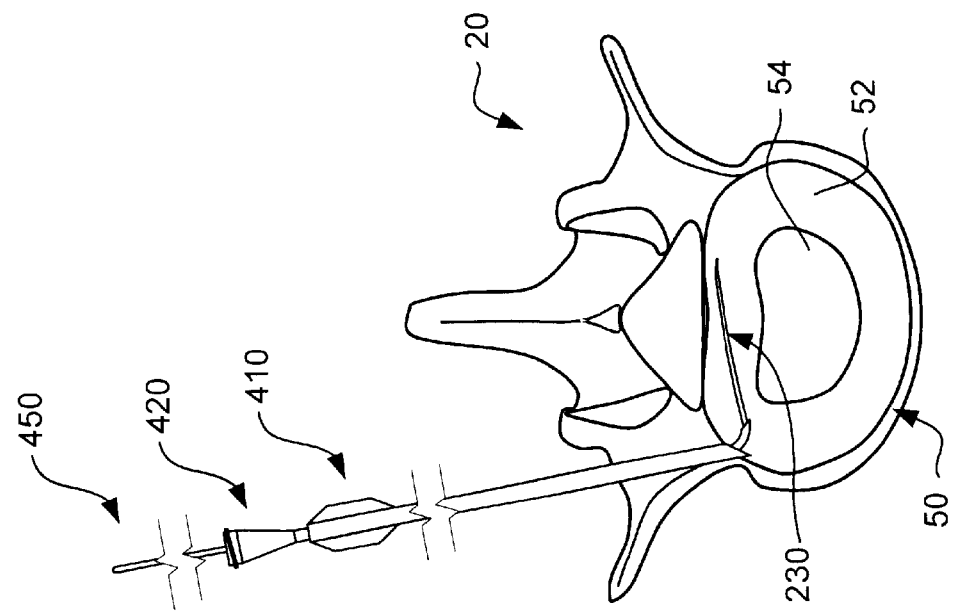
Figure 15R:
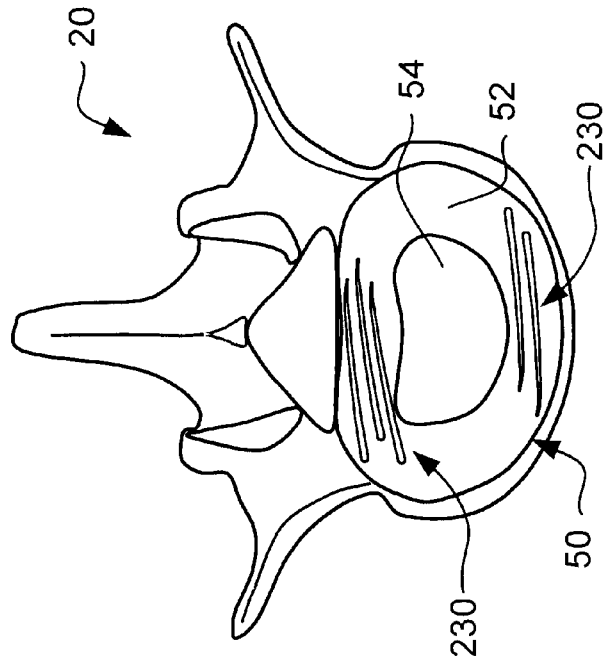

With reference to FIGS. 15M–15R, the steps for implanting a reinforcement bar 230 are illustrated. As seen in FIG. 15M, the disc 50 includes a protrusion or bulge 56, which is preferably, but not necessarily, reduced or eliminated before insertion of the reinforcement bar 230. This may be done by separating the adjacent vertebrae 20. In order to establish separation of the vertebrae 20, the spine 10 may be placed in traction or conventional intervertebral separation tools may be used. After the bulge 56 is reduced or eliminated, similar steps are followed as outlined with reference to FIGS. 15A–15C.

Delivery of a single reinforcement bar 230 into the posterior annulus 52 is illustrated. Specifically, the distal portion of the assembly 410/420/450 is inserted into the disc 50 as in a conventional discogram procedure. The assembly 410/420/450 is advanced until the distal tip 413 of the rigid needle 410 just penetrates the posterior side of the annulus 52, as seen in FIG. 15N. The semi-rigid needle 420 (alone or with bar 230) is advanced relative to the rigid needle 410 until the curved portion 426 of the semi-rigid needle 420 exits the distal tip 413 of the rigid needle 410 and the desired amount of curvature is established, as shown in FIG. 15N. The curved portion 426 may be advanced until the tip 423 is substantially parallel to the posterior annulus 52.

Figure 15Q:
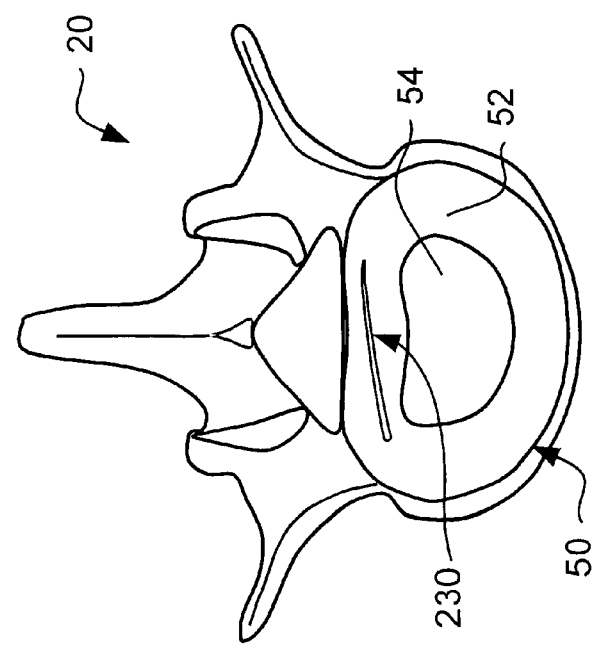

Using the push bar 450, the reinforcement bar 230 with its sharpened tip is pushed into the annulus 52 as seen in FIG. 15O. The reinforcement bar 230 is advanced into the annulus 52 with the push bar 450 until the bar 230 is in the desired position, as seen in FIG. 15P, which may be confirmed using radiographic visualization as described above. The push bar 450 is then retracted, leaving the reinforcement bar 230 in place, as shown in FIG. 15P. The semi-rigid needle 420 and the rigid needle 410 are then removed, as shown in FIG. 15Q, or, if necessary, the procedure may be repeated for additional reinforcement bar implants 230, as shown in FIG. 15R. Presence of the reinforcement bars 230 serves to keep the disc 50, and particularly the bulge 56, in a more normal condition, and to protect against continued bulging, thus easing nerve impingement.

From the foregoing, those skilled in the art will appreciate that the present invention provides dynamic bias devices 100, 110, 120, 130, 140, 150, 160, and 170, in addition to reinforcement devices 210, 220, and 230, which may be used individually or in combination, to eliminate nerve impingement associated with a damaged disc 50, and/or to reinforce a damaged disc, while permitting relative movement of the vertebrae $20_S$ and $20_I$ adjacent the damaged disc. The present invention also provides minimally invasive methods of implanting such devices as described above.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of reinforcing an annulus of an intervertebral disc disposed between a first vertebra and a second vertebra in an adult human spine, the method comprising the steps of:

providing an implantable reinforcement member; and implanting the reinforcement member into the annulus of the intervertebral disc such that the reinforcement member is completely disposed within the annulus.

2. A method as in claim 1, further comprising the step of partially separating the adjacent vertebrae prior to the step of implantation.

3. A method as in claim 1, wherein a plurality of implantable reinforcement members are provided, and wherein the plurality of reinforcement members are implanted substantially parallel in the annulus.

4. A method as in claim 1, wherein the reinforcement member is expandable, further comprising the step of expanding the reinforcement member.

5. A method as in claim 1, further comprising the steps of:
providing a tubular member having a curved tip and a lumen extending therethrough;
inserting the tip of the tubular member into the annulus; and
inserting the reinforcement member through the lumen of the tubular member and into the annulus.

6. A method as in claim 1, further comprising the steps of:
providing one or more implantable bias devices, each having a first vertebral attachment member, a second vertebral attachment member, and a bias force member applying a bias force therebetween while permitting near normal relative motion therebetween;
attaching the first attachment member of each implantable bias device to the first vertebra; and
attaching the second attachment member of each implantable bias device to the second vertebra.

7. A method as in claim 1, wherein the annulus has a peripheral curvature, and wherein the reinforcement member is implanted in a position substantially conforming to the curvature.

8. A method as in claim 1, wherein the annulus has a posterior portion with a posterior periphery, and wherein the reinforcement member is implanted in the posterior portion of the annulus in a position substantially aligned with the posterior periphery.

9. A method as in claim 1, wherein the reinforcement member applies a force to the annulus.

10. A method as in claim 9, wherein the force compresses a portion of the annulus.

11. A method as in claim 9, wherein the force is sufficient to deform the annulus.

* * * * *